(12) United States Patent
Hoffmann et al.

(10) Patent No.: US 9,387,255 B2
(45) Date of Patent: Jul. 12, 2016

(54) MODIFIED ANTIBIOTIC PEPTIDES HAVING VARIABLE SYSTEMIC RELEASE

(75) Inventors: Ralf Hoffmann, Großpösna (DE); Nicole Berthold, Leipzig (DE); Friederike Nollmann, Frankfurt am Main (DE)

(73) Assignee: UNIVERSITAET LEIPZIG, Leipzig (DE)

(*) Notice: Subject to any disclaimer, the term of this patent is extended or adjusted under 35 U.S.C. 154(b) by 0 days.

(21) Appl. No.: 14/128,083

(22) PCT Filed: Jun. 20, 2012

(86) PCT No.: PCT/EP2012/061780
§ 371 (c)(1),
(2), (4) Date: Dec. 20, 2013

(87) PCT Pub. No.: WO2012/175532
PCT Pub. Date: Dec. 27, 2012

(65) Prior Publication Data
US 2014/0309161 A1    Oct. 16, 2014

(30) Foreign Application Priority Data
Jun. 20, 2011    (DE) .................... 10 2011 118 029

(51) Int. Cl.
| | | |
|---|---|---|
| A61K 38/16 | (2006.01) |
| A61K 38/10 | (2006.01) |
| C07K 14/435 | (2006.01) |
| C07K 7/08 | (2006.01) |
| A61K 47/48 | (2006.01) |
| A01N 37/46 | (2006.01) |
| A01N 63/02 | (2006.01) |
| C12Q 1/37 | (2006.01) |
| A01N 25/22 | (2006.01) |
| A61K 38/00 | (2006.01) |

(52) U.S. Cl.
CPC .......... *A61K 47/48215* (2013.01); *A01N 25/22* (2013.01); *A01N 37/46* (2013.01); *A01N 63/02* (2013.01); *A61K 38/10* (2013.01); *A61K 38/16* (2013.01); *C07K 7/08* (2013.01); *C07K 14/43563* (2013.01); *C12Q 1/37* (2013.01); *A61K 38/00* (2013.01)

(58) Field of Classification Search
None
See application file for complete search history.

(56) References Cited

U.S. PATENT DOCUMENTS

| 4,179,337 | A | 12/1979 | Davis et al. |
|---|---|---|---|
| 5,965,119 | A | 10/1999 | Greenwald et al. |
| 6,180,095 | B1 | 1/2001 | Greenwald et al. |
| 6,303,569 | B1 | 10/2001 | Greenwald et al. |
| 6,720,306 | B2 | 4/2004 | Greenwald et al. |
| 7,291,673 | B2 | 11/2007 | Hubbell et al. |
| 7,585,837 | B2 | 9/2009 | Shechter et al. |
| 2002/0041898 | A1* | 4/2002 | Unger et al. ................. 424/486 |
| 2003/0008820 | A1* | 1/2003 | Kwan ................... C07K 14/50 514/9.1 |
| 2004/0192769 | A1 | 9/2004 | Greenwald et al. |
| 2005/0003485 | A1* | 1/2005 | Gruenbeck ............ C12P 21/02 435/69.1 |
| 2005/0215470 | A1 | 9/2005 | Ng et al. |
| 2008/0014149 | A1 | 1/2008 | Murthy et al. |
| 2010/0150843 | A1* | 6/2010 | Johannesen et al. ............ 424/9.6 |
| 2013/0330335 | A1* | 12/2013 | Bremel ................... G06F 19/18 424/134.1 |

FOREIGN PATENT DOCUMENTS

| CA | 2751010 A1 * | 8/2010 |
|---|---|---|
| DE | 10 2009 007 381 A1 | 8/2010 |
| EP | 1897561 A1 | 3/2008 |
| WO | 99/30727 A1 | 6/1999 |
| WO | 02/43663 A1 | 6/2002 |
| WO | 2009/013262 A1 | 1/2009 |
| WO | 2010/072752 A2 | 7/2010 |

OTHER PUBLICATIONS

Sang et al., "Porcine host defense peptides: Expanding repertoire and functions", Developmental and Comparative Immunology, 2009, pp. 334-343.*

Ryan et al., "Advances in PEGylation of important biotech molecules: delivery aspects", Expert Opin. Drug Deliv., 2008; pp. 371-383.*

Boman, H.G.: Peptide antibiotics and their role in innate immunity; Annu. Rev. Immunol. 1995 13:61-92.

Barra, D. et al.: Gen-encided petide antibiotics and innate immunity; FEBS Letters 430 (1998) 130-134.

Otvos, L. et al.: Insect peptides with improved protease-resistance protect mice against bacterial infection; Protein Science (2000) 9:742-749.

(Continued)

*Primary Examiner* — Lianko Garyu
(74) *Attorney, Agent, or Firm* — FisherBroyles, LLP; Andrew K. Gonsalves, Esq.

(57) ABSTRACT

The invention relates to modified antibiotic peptides, in particular derivatives of apidaecin and oncocin, preferably having increased stability, reduced immunoreaction, and improved pharmacokinetics. In the invention, the peptide antibiotics are reversibly protected by means of a linker having the polymer polyethylene glycol (PEG). The peptide linker contains a recognition sequence for trypsin-like serum proteases. In the apidaecin derivatives, the linker and the PEG are bonded to a side chain. In the serum, the linker is cut by serum proteases and PEG is separated off. The released peptide still contains remnants of the linker, which are still bonded to the amino group in the side chain. Astonishingly, said remaining remnants of the linker impair the activity of the antimicrobial peptide only a little or not at all.

8 Claims, 10 Drawing Sheets

(56) References Cited

OTHER PUBLICATIONS

Schneider M. et al.: Differential infectivity of two *Pseudomonas* species and the immune response in the milkweed bug Oncopeltus fasciatus (insecta: hemiptera) J Invertebr Pathol. 78, 135-140 (2001).
Yang J et al.: Synthesis and characterization of enzymatically degradable PEG-based peptide-containing hydrogels; Macromol. Biosc. 2010, 10, 445-454.
Kodera, M et al. Pegylation of proteins and bioactive substances for medical and technical applications; Prog Polym Sci. 23:1233-1271, 1998.
Veronese FM, et al.: Introduction and overview of peptide and protein pegylation; Advanced Drug Delivery Reviews 54 (2002) 453-456.
Veronese FM et al.: PEG-doxorubicin conjugates: Influence of polymer structures on drug release, in vitro cytotoxity, biodistribution, and antitumor activity; Bioconjugate Chem: 2005, 16, 775-784 (see international search report).
Veronese FM: Peptide and protein PEGylation: a review of problems and solutions; Biomaterials 22 (2001) 405-417.
Roberts MJ et al.; Chemistry for peptide and protein PEGylation; Advanced Drug Delivery Reviews 54 (2002) 459-476.
Greenwald RB et al.: Drug delivery systems employing 1,4-elimination or 1,6-elimination: poly(ethylene glycol) prodrugs of amine-containing compounds; J. Med. Chem. 1999, 42, 3657-3667.
Lee S et al.: Drug delivery systems employing 1,6-elimination: releasable poly(ethylene glycol) conjugates of proteins; Bioconjugate Chem. 2001, 12, 163-169.
Greenwald RB et al.; Controlled release of proteins from their poly(ethylene glycol) conjugates: drug delivery systems employing 1,6-elimination; Bioconjugate Chem. 2003, 14, 395-403.
Guiotto A et al.; Synthesis, characterization, and preliminary in vivo tests of new poly(ethylene glycol) conjugates of the antitumor agent 10-amino-7-ethylcamoptothecin; J. Med. Chem. 47, 1280-1289, 2004.
Law B et al.: Proteolysis: a biological process adapted in drug delivery, therapy, and imgaing; Bioconjugate Chem. 2009, 20(9):1683-1695; see international search report.
Li H et al.: A protease-based strategy for the controlled release of therapeutic peptides; Angew. Chem. Int. Ed. 2010, 49, 4930-4933; see international search report.
Filpula D et al.: Releasable PEGylation of proteins with customized linkers; Advanced Drug Delivery Reviews 60 (2008) 29-49; see international search report.
Maeno M et al.: Production of antibacterial peptide "apidaecin" using the secretory expression system of Streptomyces; Biosci. Biotech. Biochem., 57 (7), 1206-1207, 1993.
Noren C. et al.: A general method for site-specific incorporation of unnatural amino acids into proteins; Science, vol. 244, pp. 182 ff, 1989.
Knappe D et al: Rational design of oncocin derivatives with superior protease stabilities and antibacterial activities based on the high-resolution strcuture of the oncocin-Dnak complex; ChemBioChem 2011, 12, 874-876.
Li H et al.: A protease-based strategy for the controlled release of therapeutic peptides; Angew. Chem. 2010, 122, 5050-5053.
Ellman J. et al.: Biosynthetic method for introducing unnatural amino acids site-specifically into proteins; Methods in Enzymology, vol. 202, pp. 301ff (1991).
Dupont E. et al.: Chapter 1: Penetratins; in Handbook of cell-penetrating peptides; pp. 5-28; Editor: Ülo Langel; CRC Press,Taylor & Francis Group, Boca Raton, FL, USA; 2002.

\* cited by examiner

MODIFIED ANTIBIOTIC PEPTIDES HAVING VARIABLE SYSTEMIC RELEASE

BACKGROUND OF THE INVENTION

This invention relates to modified antibiotic peptides in particular for use in medicine. The invention relates also to compositions and methods for killing microorganisms, such as bacteria, viruses or fungi, and to methods for treating microbial infections.

The occurrence of serious bacterial and fungal infections is an increasing problem despite remarkable progress in antibiotic therapy. Each year there are more than 40 million hospital stays in the United States of America, and more than 2 million of those patients become infected in hospital. In 50-60% of these cases, antibiotic-resistant bacteria are involved. It is estimated that such diseases acquired in hospital lead to 60,000-70,000 deaths in the USA and up to 10,000 deaths in Germany.

This illustrates the necessity to continue the search for new antibiotics. Inducible antibacterial peptides represent a research area in which current biochemistry, immunology and active ingredient research come together. Peptide antibiotics, with a size of from 13 to more than a hundred amino acids, have been isolated from plants, animals and microbes (Boman, H. G. 1995 Annu. Rev. Immunol. 13: 61-92).

A single animal possesses about 6-10 antimicrobial peptides, each peptide often exhibiting a completely different activity spectrum (Barra, D. et al., 1998. FEBS Lett. 430: 130-134). It is known that the majority of antibacterial peptides, including the widely studied defensins, cecropins and magainins, act by a "lytic/ionic" mechanism. A permeabilising effect on the bacterial cytoplasm membrane is discussed as a common mechanism of action of these "lytic" peptides. A cationic, amphipathic structure, which forms hydrophilic ion (proton) channels in a lipid bilayer, is the basis for this activity. Through the occurrence of ions, the membrane potential necessary for many fundamental life processes is destroyed and the cell is thus killed. These lytic peptides often have a toxic effect on mammalian membranes at higher concentrations, which limits their suitability as possible medicaments. If proline is inserted into the sequence of the α-helical antimicrobial peptides, the ability of the peptides to permeabilise the cytoplasm membrane of E. coli falls, in dependence on the number of praline residues. From this point of view, it is amazing that some of the most active, natural antibacterial peptides, at least in relation to some gram-negative pathogens, belong to the family of the proline-rieh peptides (Otvos, L. et al. 2000. Protein Sci. 9: 742-749).

The above-described side-effects could be overcome by antimicrobial peptides (AMP) which specifically recognise a bacterial protein or other intra- or extra-cellular components, without exhibiting cross-reactivity with mammalian analogs. This appears to apply to proline-rich antimicrobial peptides, including apidaecins, drosocin and pyrrhocoricin, which were originally isolated from insects. With the enormous variation in the size and biochemical properties, it is not surprising that the structure-action and conformation-action relationships are the focus of antibacterial peptide research. A complete study of the natural, antibacterial peptide repertoire for biological strength is not only important for general biochemical questions but is also of sustained interest for the pharmaceutical industry. Despite the problems of in vitro tests with peptide-based antibiotics, some natural, cationic antibacterial peptides have already reached the clinical trial phase (Boman, H. G. 1995 ebd.). While some of these peptides exhibited activity as topical (local) agents in the early clinical trial phase, others were active in systemic therapy. For example, the cationic protein rBPI 21, which is used for the parenteral treatment of meningococcemia, has completed the third phase of clinical testing (Boman, H. G. 1995 ebd.).

The family of the proline-rich peptides (e.g. apidaecin, drosocin and pyrrhocoricin) kill bacteria not by permeabilisation of their membrane but bind stereospecifically to one or more target proteins. These possible interaction partners, the heat shock protein DnaK has hitherto been thoroughly researched (inter alia Boman, H. G. 1995), are inhibited by the proline-rich peptides and presumably the correct protein folding is inhibited, which ultimately leads to cell death. In addition, proline-rich peptides, in stark contrast to AMPs with a defined secondary structure such as melittin or gramicidin, do not appear in vitro to act either haemolytically or toxically on eukaryotic cells. In addition to the antimicrobial activity, the stability in mammalian serum (25%) especially has a decisive influence on the development of new peptide-based antibiotics. For example, drosocin is degraded within an hour, while pyrrhocoricin, with half-lives of 120 minutes, is considerably more stable to proteases. Presumably, not only are the N- and C-termini cleaved by amino and carboxy peptidases, but the peptides are also digested by endoproteases. Some of the metabolites formed thereby are stable to further decomposition but in most cases lose the antimicrobial activity (MIC values ≥64 µg/ml).

In experiments conducted by Schneider M. and Dorn A. (2001. J Invertebr Pathol. 78: 135-40), nymphs and pupae of the large milkweed bug Oncopeltus fasciatus from the family of the Lygaeidae were infected with two different gram-negative Pseudomonas species, and their immune response was analysed. While infection of the nymphs of O. fasciatus with the human pathogen Pseudomonas aeruginosa resulted in the death of all individuals after 48 hours, 71% of the individuals infected with the less pathogenic Pseudomonas putida survived for at least 96 hours. If the nymphs of the large milkweed bug were infected first with P. putida and after 24 hours with P. aeruginosa, the survival rate of the doubly infected individuals within the first 24 hours increased significantly to 73%. The probable induction of the synthesis of antibacterial peptides, by means of which insects defend themselves against incoming microorganisms within the context of their innate immune system, was then investigated. Four peptides (oncopeltus antibacterial peptide 1-4) were identified with molecular weights of 15, 8, 5 and 2 kDa and made responsible for the antibacterial activity. Sequence analysis according to Edman revealed, in addition to a partial sequence 34 amino acids long for peptide 1 (15 kDa), also the incomplete sequence of the proline-rich 2 kDa peptide 4. It was not possible clearly to identify the amino acids at positions 11 and the C-terminal sequence from position 19. The exact molecular weight is unknown.

A selection of hitherto known sequences of antibiotic peptides is listed in Table 1:

TABLE 1

| Peptide | Species | Sequence | SEQ ID No. |
|---|---|---|---|
| Apidaecin 1a | Apis mellifera | GNNRPVYIPQPRPPH PRI | 1 |
| Apidaecin 1b | Apis mellifera | GNNRPVYIPQPRPPH PRL | 2 |

TABLE 1-continued

| Peptide | Species | Sequence | SEQ ID No. |
|---|---|---|---|
| Drosocin | Drosophila melanogaster | GKPRPYSPRPTSHPRP IRV | 3 |
| Formaecin 1 | Myrmecia gulosa | GRPNPVNNKPTPYPHL | 4 |
| Pyrrhocoricin | Pyrrhocoris apterus | VDKGSYLPRPTPPRPIY NRN-NH$_2$ | 5 |
| Metalnikowin 1 | Palomena prasina | VDKPDYRPRPRPPNM | 6 |
| Oncopeltus antibacterial peptide 1 | Oncopeltus fasciatus | EVSLKGEGGSNKGFIQG SGTKTLFQDDKTKLDGT | 7 |
| Oncopeltus antibacterial peptide 4 | Oncopeltus fasciatus | VDKPPYLPRP(X/P)PP RRIYN(NR) | 8 |

Apidaecin derivatives are disclosed in WO2009013262A1. Derivatives of oncopeltus antibacterial peptide 4 are disclosed in WO2010086401A1.

Different approaches at influencing the pharmacokinetic properties of pharmacological active ingredients are described in the literature. Organic polymers (such as e.g. polyethylene glycol) are also used thereby.

The use of polyethylene glycol (PEG) in pharmaceutical dosage forms for the controlled release of an active ingredient is known. A distinction must be made between two forms:
1. The introduction of the active ingredient into a crosslinked PEG hydrogel;
2. The direct bonding of a linear or branched PEG molecule to the active ingredient (known as PEGylation).

The two forms differ not only in the pharmacokinetics but also especially in the possible administration routes. The hydrogel is administered locally. The PEGylated active ingredient is administered systemically (generally intravenously).

Hydrogels for the controlled release of an active ingredient are known inter alia from U.S. Pat. No. 7,291,673, US 2008/0014149 A1 and Yang J et al. 2010 (Macromol. Biosci., 10, 445-454).

The PEGylation of polypeptides is used in particular in order on the one hand to achieve controlled release over a desired period of time (retard effect) and on the other hand to delay the excretion of the active ingredient via the kidneys.

For the PEGylation of pharmaceutical active ingredients, reference may be made inter alia to U.S. Pat. No. 4,179,337, and also to the overview articles Kodera, M et al. 1998 (Prog Polym Sci. 23: 1233-71) and Veronese F M, Harris J M 2002 (Adv Drug Deily Rev 54: 453-456).

Because an irreversible bonding of PEG impairs the pharmacological action of the active ingredient, a large number of known approaches for irreversible PEGylation exist.

Veronese F M (2001. Biomaterials 22: 405-17) describes in a general overview article the reversible PEGylation inter alia enzyme-catalysed to glutamine side chains by the enzyme transglutaminase. In an overview article by Roberts M J et al. 2002 (Adv Drug Deliv Rev 54: 459-476) too, several techniques for reversible PEGylation of peptides and proteins are mentioned, in particular hydrolysable ester bridges, reducible disulfide bridges.

EP1897561A, WO9930727, U.S. Pat. No. 6,180,095, U.S. Pat. No. 6,720,306, WO0243663 describe the use of a linker, which is cleaved by a 1,4- or 1,5-benzyl elimination. In several publications, this linker is combined in what is known as a double prodrug approach with an enzymatically cleavable group or a hydrolysable ester group (Greenwald R B et al. 1999. J. Med. Chem. 42: 3657-3667; Lee S of al. 2001 Bioconjug Chem 12, 163-169; Greenwald R B et al. 2003. Bioconjug Chem. 14(2): 395-403).

Another approach to reversible PEGylation is trimethyl lock lactonization (TML), which is disclosed inter alia in U.S. Pat. No. 5,965,119 and U.S. Pat. No. 6,303,569.

U.S. Pat. No. 7,585,837 describes an approach to reversible PEGylation by derivatisation of functional groups with 9-fluorenylmethoxycarbonyl (Fmoc) or 2-sulfo-9-fluorenylmethoxycarbonyl (FMS), which are readily cleaved by bases.

Guiotto et al. 2004 (J. Med. Chem. 47: 1280-9) describes the synthesis, characterisation and first in vivo tests of PEG conjugates of the antitumour agent 10-amino-7-ethylcamptothecin.

A protease-based prodrug strategy is based on peptide linkers which are bonded to conventional chemical active ingredients ("small molecules") and contain cutting sites for proteases. The proteases that are used are mainly tissue-specific proteases or proteases which play a part in tissue remodelling (such as e.g. Cathepsin B, PSA (prostate specific antigen) and matrix metalloproteases (MMP), but also the serum proteases plasmin and urokinase. The field of application of the active ingredients is substantially cancer therapy. The protease cutting site is used for tumour targeting. In this connection, reference may be made to the overview article of Law B, Tung C H. 2009 (Bioconjug Chem. 20(9):1683-95). US 2004192769 mentions the approach of configuring the drug delivery system in such a manner that the peptide linker is cleaved not by serum proteases but only after being taken up into the target cell.

Li H et al. A 2010 (Angew. Chem. Int. Ed. 49, 4930-4933) apply a protease-based prodrug strategy to peptide active ingredients. Therapeutically active peptides are bonded via the peptide linker to an albumin binding domain (ABD). In the blood, this fusion peptide first binds to the serum protein albumin and is then cleaved by the protease thrombin (or human factor Xa).

There is a continued need for new antibiotics.
Desirable properties for peptide antibiotics are:
(i) an increased half-life in mammalian serum through a higher protease resistance and
(ii) unchanged or preferably increased antimicrobial activity against one or more bacterial strains, particularly human pathogens, or fungi or other microbial infections,
(iii) a reduced antigenic action and, as a result, a reduced immune reaction, and
(iv) the peptides are not toxic to human cells, including erythrocytes.

The action of proline-rich antimicrobial peptides is very complex, because they must penetrate the cell membrane and pass into the cytoplasm in order to inhibit a specific intracellular bacterial target molecule, but without having a toxic effect on mammalian cells and blood cells. Another important point is the stability of the peptides or peptide derivatives to degradation by peptidases or proteases in blood and the bacteria. The ideal peptide therefore has a high antibacterial activity (low MIC values), no cell toxicity, no haemolytic activity and a half-life of several hours in blood.

It is an object of the invention to provide novel peptide antibiotics, preferably having increased stability, reduced immune reaction and improved pharmacokinetics.

SUMMARY OF THE INVENTION

In the invention, peptide antibiotics are reversibly protected by the polymer polyethylene glycol (PEG) via an enzymatically cleavable peptide chain, in order to reduce the degradation of the active ingredient in serum by proteases and the toxicity of the active ingredient, as well as to achieve a longer dwell time in the organism (improved pharmacokinetics). The active ingredients are released from this chemically defined compound by the proteases of the host (e.g. patient, in particular serum proteases) or the bacteria. The choice according to the invention of the polymer (structure, length) and of the peptide linker (length, sequence) allows the kinetics of the active ingredient release to be adapted to the mechanism of action of the active ingredient and its metabolisation or excretion. Thus, by a clever choice of structure (polymer, linker), a constant concentration of the active ingredient can be achieved over a prolonged treatment period.

According to the invention, the object is achieved in a first aspect by a modified peptide, an apidaecin derivative, which has a sequence according to the general formula 1, 2 or 3:

NT-X$_1$X$_2$NX$_3$PVYIPX$_4$X$_5$RPPHP-CT (SEQ ID No. 67)  (formula 1)

NT-X$_1$NX$_2$X$_3$PVYIPX$_4$X$_5$RPPHP-CT (SEQ ID No. 68)  (formula 2)

NT-X$_2$NNX$_3$PVYIPX4X$_5$RPPHP-CT (SEQ ID No. 69)  (formula 3)

wherein X$_1$ is an amino acid residue whose side chain is positively charged under physiological conditions, preferably O (ornithine),
wherein X$_2$ is an amino acid residue having an amino group in the side chain,
wherein X$_3$ is an amino acid residue whose side chain is positively charged under physiological conditions, preferably R (arginine),
wherein X$_4$ is an amino acid residue whose side chain is positively charged under physiological conditions, preferably R,
wherein X$_5$ is proline or a proline derivative,
wherein CT is the C-terminus or a peptide having from 1 to 4 amino acid residues, preferably a dipeptide having the sequence RL (Arg-Leu),
wherein NT is the N-terminus, which is preferably guanidated.

The remaining amino acid residues each have the meaning according to the IUPAC one-letter code.

Modified peptides according to formulae 1 and 2 are particularly preferred.

The modified peptide according to the invention is characterized in that a linear or branched polyethylene glycol polymer chain is bonded via a peptide linker to the amino group in the side chain of X$_2$, and the peptide linker is from 3 to 10 amino acid residues long and contains at least one arginine or lysine.

X$_2$ is preferably an L-ornithine.

The peptide linker contains a recognition sequence for trypsin-like serum proteases and is preferably selected from linkers having from 4 to 10 amino acid residues which contain at least one arginine or lysine. The linker preferably has the following general formula:

(L$_1$)$_n$-R-(L$_2$)$_m$ or (L$_1$)$_n$-K-(L$_2$)$_m$ wherein n and m are integers from 1 to 8 and n+m is from 3 to 9,
wherein the individual L$_1$ and L$_2$ are selected independently of one another from amino acids having from 2 to 6 carbon atoms, preferably 2 or 3 carbon atoms, in particular glycine, alanine and serine. Particularly preferably, m=2 or 3. Preferably, (L$_2$)$_m$=SG.

More preferably, the linker has the following formula:

G(L)$_k$RSG where L is selected from alanine, glycine and serine and k is selected from integers from 1 to 6, preferably 1, 2, 3 or 4.

Particularly preferred linkers are selected from the peptides GRSG, GARSG, GAARSG, GAAARSG and GAAAARSG (SEQ ID No. 61 to 65). The polyethylene glycol polymer chain is preferably bonded to the alpha-amino group of the first amino acid residue of the linker, preferably a glycine. The carboxyl group of the last amino acid residue of the linker is bonded to the amino group in the side chain of X$_2$ (preferably the delta-amino group of an L-ornithine residue). Trypsin and related serum proteases each cut downstream of the R (or K) in the peptide linker, so that the peptide is released from the polyethylene glycol polymer chain. The released peptide still contains the amino acid residues of the linker which were originally located to the right (C-terminal) of the R (or K), these are preferably the amino acid residues SG. These residues of the linker remaining in the released peptide are still bonded to the amino group in the side chain of X$_2$ (preferably the delta-amino group of an L-ornithine residue).

Surprisingly, these remaining residues of the linker do not impair or scarcely impair the activity of the antimicrobial peptide (apidaecin derivative).

Particularly preferred modified peptides (apidaecin derivatives) have the following peptide sequences:

ONORPVYIPRPRPPHPRL (SEQ ID No. 9)
or
OONRPVYIPRPRPPHPRL (SEQ ID No. 10)
where O = L-ornithine wherein the alpha-amino group of the first ornithine is guanidated and a linear or branched polyethylene glycol polymer chain is bonded to the delta-amino group of the second ornithine via a peptide linker chosen as above, preferably selected from GRSG, GARSG and GAARSG (SEQ ID No. 61 to 63).

Preliminary tests showed that a modification of the C-terminus leads to a large activity loss. A certain activity loss is observed on incorporation of the side chain at, position 1 (formula 3, Orn-1 in SEQ ID No. 11), therefore the substitution of Asn-2 and Asn-3 for Orn (SEQ ID No. 9 and 10) is particularly preferred.

Somewhat less preferred modified peptides (apidaecin derivatives) have the following peptide sequence:

ONNRPVYIPRPRPPHPRL (SEQ ID No. 11)
where O = L-ornithine wherein the alpha-amino group of the first ornithine is guanidated and a linear or branched polyethylene glycol polymer chain is bonded to the delta-amino group of the same ornithine via a peptide linker selected from GRSG, GARSG and GAARSG (SEQ ID No. 61 to 63).

Preferred modified peptides have the following structures:

PEG$^{750}$-linker 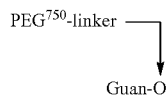

Guan-ONNRPVYIPRPRPPHPRL—OH (SEQ ID NO. 78)

-continued

PEG$^{5000}$-linker ⎯⎯⎯┐
                       ↓
        Guan-ONNRPVYIPRPRPPHPRL⎯OH    (SEQ ID NO. 79)

PEG$^{750}$-linker ⎯⎯⎯┐
                      ↓
        Guan-OONRPVYIPRPRPPHPRL⎯OH    (SEQ ID NO. 80)

PEG$^{5000}$-linker ⎯⎯⎯┐
                       ↓
        Guan-OONRPVYIPRPRPPHPRL⎯OH    (SEQ ID NO. 81)

PEG$^{750}$-linker ⎯⎯⎯┐
                      ↓
        Guan-ONORPVYIPRPRPPHPRL⎯OH    (SEQ ID NO. 82)

PEG$^{5000}$-linker ⎯⎯⎯┐
                       ↓
        Guan-ONORPVYIPRPRPPHPRL⎯OH,   (SEQ ID NO. 83)

wherein linker represents the peptide linker, which is chosen as above, particularly preferably GRSG (SEQ ID NO. 61).

The invention further provides a modified peptide derived from *oncopeltus* antibacterial peptide 4, which has a sequence according to one of the general formulae 4 to 6:

$$\text{NT-}X_1\text{-}D_2\text{-}K_2\text{-}P_4\text{-}P_5\text{-}Y_6\text{-}L_7\text{-}P_8\text{-}R_9\text{-}P_{10}\text{-}X_2\text{-}P_{12}\text{-}P_{13}\text{-}R_{14}\text{-}X_3\text{-}I_{16}\text{-}Y_{17}\text{-}N_{18}\text{-}X_4\text{-CT (SEQ ID No. 71)} \quad \text{(formula 4)}$$

$$\text{NT-}X_1\text{-}D_2\text{-}K_3\text{-}P_4\text{-}P_5\text{-}Y_6\text{-}L_7\text{-}P_8\text{-}R_9\text{-}P_{10}\text{-}X_2\text{-}P_{12}\text{-}P_{13}\text{-}R_{14}\text{-}X_3\text{-}I_{16}\text{-}Y_{17}\text{-}N_{18}\text{-}N_{19}\text{-}X_4\text{-CT (SEQ ID No. 72)} \quad \text{(formula 5)}$$

$$\text{NT-}X_1\text{-}D_2\text{-}K_3\text{-}P_4\text{-}P_5\text{-}Y_6\text{-}L_7\text{-}P_8\text{-}R_9\text{-}P_{10}\text{-}X_2\text{-}P_{12}\text{-}P_{13}\text{-}R_{14}\text{-}X_3\text{-}I_{16}\text{-}P_{17}\text{-}N_{18}\text{-}X_4\text{-CT (SEQ ID No. 73)} \quad \text{(formula 6)}$$

$X_1$ is a residue having a non-polar, hydrophobic side chain or an amino acid residue whose side chain is positively charged under physiological conditions, having a positive net charge or a side chain that is positively charged under physiological conditions;

$D_2$ is an aspartic acid or glutamic acid residue, $K_3$ is a residue having a positive net charge or a side chain that is positively charged under physiological conditions, preferably lysine or arginine, $X_2$ and $X_4$ are selected independently of one another from residues having a positive net charge or a side chain that is positively charged under physiological conditions;

$X_3$ is a radical having a positive net charge or a side chain that is positively charged under physiological conditions or proline or a proline derivative;

$L_7$ and $I_{16}$ are selected independently of one another from residues having a non-polar, hydrophobic side chain, preferably leucine, isoleucine, valine and tert-leucine, $Y_6$ and $Y_{17}$ are each tyrosine, $R_9$ and $R_{14}$ are each arginine, $N_{18}$ and $N_{19}$ are each asparagine or glutamine, $P_4$, $P_5$, $P_8$, $P_{10}$, $P_{12}$, $P_{13}$ and $P_{17}$ are selected independently of one another from proline and proline derivatives or hydroxyproline and hydroxyproline derivatives, wherein $P_{13}$ and $R_{14}$ are optionally interchanged, and/or optionally one or two residues selected from $D_2$, $P_4$, $P_5$, $P_8$, $P_{10}$, $P_{12}$ $P_{13}$, $P_{17}$ and $Y_{17}$ are replaced by any desired residue, NT is the N-terminus of the amino acid $X_1$, CT is the free C-terminal carboxyl group of the C-terminal amino acid (—COOH) or a modified C-terminal carboxyl group.

This peptide (oncopeltus peptide derivative) is distinguished in that a linear or branched polyethylene glycol polymer chain is bonded via a peptide linker to NT, wherein the peptide linker is from 2 to 10 amino acid residues long and contains at least one arginine or lysine.

The linker preferably has the following general formula:

$$(L_1)_n\text{-R or }(L_1)_n\text{-K}$$

wherein n is an integer from 1 to 9 and the individual $L_1$ are selected independently of one another from amino acids having from 2 to 6 carbon atoms, preferably 2 or 3 carbon atoms, in particular glycine, alanine and serine. Particularly preferably, n=1 to 3.

More preferably, the linker has the following formula:

$$G(L)_k R \quad \text{(SEQ ID No. 74)}$$

where L is selected from alanine, glycine and serine and k is selected from 1, 2 and 3.

Particularly preferred linkers are selected from the peptides GR, GAR and GAAR (SEQ ID No. 66).

$X_5$ and $X_6$ are optionally additional residues. Where $X_5$ and $X_6$ are absent, the last arginine (Arg) in the above-mentioned sequence has a free C-terminal carboxyl group or is bonded to CT.

Where at least one residue $X_5$ and $X_6$ is present, the peptide has, for example, a sequence according to one of the general formulae 7 to 9:

$$\text{NT-}X_1\text{-D-K-P-P-Y-L-P-R-P-}X_2\text{-P-P-R-}X_3\text{-I-Y-N-}X_4\text{-}X_5\text{-}X_5\text{—COR}_3 \text{ (SEQ ID No. 75)} \quad \text{(formula 7)}$$

$$\text{NT-}X_1\text{-D-K-P-P-Y-L-P-R-P-}X_2\text{-P-P-R-}X_3\text{-I-Y-N-}X_4\text{-}X_5\text{—COR}_3 \text{ (SEQ ID No. 76)} \quad \text{(formula 8)}$$

$$\text{NT-}X_1\text{-D-K-P-P-Y-L-P-R-P-}X_2\text{-P-P-R-}X_3\text{-I-Y-N-}X_4\text{-}X_6\text{—COR}_3 \text{ (SEQ ID No. 77)} \quad \text{(formula 9)}$$

$X_5$ is selected from proline, proline derivatives or a neutral residue having a polar side chain (such as asparagine, glutamine). Preferred residues $X_5$ are selected from the groups comprising proline, cis-4-hydroxyproline, trans-4-hydroxyproline, cis-3-hydroxyproline, trans-3-hydroxyproline, β-cyclohexylalanine, 3,4-cis-methanoproline, 3,4-dehydroproline, homoproline, pseudoproline as well as asparagine, glutamine, citrulline, N-methylserine, N-methylglycine, dihydroxyphenylalanine, N-ethylasparagine, N-ethylglycine, homoserine, penicillamine, tetrahydropyranylglycine, allo-threonine and 3,5-dinitrotyrosine.

$X_6$ is selected from proline, praline derivatives, a polar residue (such as serine) or a hydrophobic residue. Preferred residues $X_6$ are selected from the groups comprising praline, cis-4-hydroxyproline, trans-4-hydroxyproline, cis-3-hydroxyproline, trans-3-hydroxyproline, β-cyclohexylalanine, 3,4-cis-methanoproline, 3,4-dehydroproline, homoproline or pseudo-praline, serine, threonine, δ-hydroxylysine, citrulline, homoserine or allo-threonine as well as phenylalanine, N-methylleucine, leucine, isoleucine, valine, methionine, tert-butylglycine, cyclohexylalanine, alanine, β-alanine, 1-aminocyclohexylcarboxylic acid, N-methylisoleucine, narleucine, norvaline, N-methylvaline, or it is a short peptide sequence having preferably from one to three residues, which are preferably selected from proline, isoleucine or one of the residues mentioned above.

Alternatively, $X_6$ is a branched linker which contains a plurality of peptide units. This is formed by the residue of an amino acid which contains a plurality of amino groups, such as, for example, lysine, hydroxylysine, ornithine, 2,4-diaminobutyric acid, 2,3-diaminopropionic acid, 2,2'-diaminopimelic acid, desmosine, isodesmosine.

The C-terminal amino acid is, for example, $X_4$ in formula 1, $X_5$ (in formula 3) or $X_6$ (in formulae 2 and 4).

Particularly preferred modified peptides (oncopeltus peptide derivatives) contain the following peptide sequences:

```
                                                  (SEQ ID No. 12)
VDKPPYLPRPRPPROIYNO-NH2
or
                                                  (SEQ ID No. 13)
VDKPPYLPRPRPHypRHypTleYNO-NH2
where O = L-ornithine, Hyp = L-4-hydroxyproline
and Tle = L-tertiary-leucine (L-tertiary-
butylglycine),
``` wherein a linear or branched polyethylene glycol polymer chain is bonded via the peptide linker, preferably GAR, to the N-terminal amino group (alpha-amino group of the first amino residue V). The C-terminus (CT) is here a carboxylic acid amide (i.e. the carboxyl group of the last ornithine has been converted into the amide).

The comments and preferred variants mentioned below apply generally to all the modified peptides according to the invention (apidaecin derivatives and oncopeltus peptide derivatives):

The modified peptides according to the invention preferably contain at least 18 amino acid residues, preferably up to 50 amino acid residues.

For all the modified peptides according to the invention (apidaecin derivatives and oncopeltus peptide derivatives), the polyethylene glycol polymer chain preferably has a molecular weight of from 500 to 40,000 Da, particularly preferably at least 5000 Da. The polyethylene glycol polymer chain is in each case bonded covalently to the peptide linker, preferably to the N-terminal amino group of the linker, particularly preferably the alpha-amino group of the glycine. Coupling to the peptide linker is carried out either directly (e.g. with an NHS ester-activated polyethylene glycol to the amino group) or by means of a short organic linker (preferably C1 to C10) and/or by formation of a thioether bond (e.g. by derivatisation of the N-terminal amino group of the linker, particularly preferably the alpha-amino group of the glycine, with iodoacetic acid and reaction with a thiol-modified polyethylene glycol). The polyethylene glycol polymer chain is preferably linear.

In all the peptides according to the invention, the tryptic cutting site is inserted immediately between the polymer and the antimicrobial peptide. An additional cleavable group, which is removed, for example, by 1,6-elimination, is not present.

Residues having a side chain that is positively charged under physiological conditions are preferably selected from arginine, lysine, δ-hydroxylysine, homoarginine, 2,4-diaminobutyric acid, 3-homoarginine, D-arginine, arginal (—COOH in arginine is replaced by —CHO), 2-amino-3-guanidinopropionic acid, nitroarginine (preferably N(G)-nitroarginine), nitrosoarginine (preferably N(G)-nitrosoarginine), methylarginine (preferably N-methyl-arginine), ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexinic acid, p-aminobenzoic acid and 3-aminotyrosine and, less preferably, histidine, 1-methylhistidine and 3-methylhistidine. $X_1$, $X_2$ and $X_3$ are preferably selected independently of one another from this list.

The expression 'praline derivative' denotes an amino acid residue derived from praline, which is obtained from proline preferably by structural alteration of a functional group. Preferred proline derivatives are selected from β-cyclohexylalanine, 3,4-cis-methanoproline, 3,4-dehydroproline, homoproline or pseudoproline. The term hydroxyproline includes inter alis cis-4-hydroxyproline, trans-4-hydroxyproline, cis-3-hydroxyproline and trans-3-hydroxyproline. The expression hydroxyproline derivative correspondingly denotes an amino acid residue derived from hydroxyproline, which is obtained from hydroxyproline preferably by structural alteration of a functional group. Preferred hydroxyproline derivatives are selected from hydroxy-β-cyclohexylalanine and the above-mentioned praline derivatives, which are substituted by a hydroxyl group.

A neutral residue is a residue having a side chain that is uncharged under physiological conditions.

A polar residue preferably has at least one polar group in the side chain. These are preferably selected from hydroxyl, sulfhydryl, amine, amide and ester groups or other groups which permit the formation of hydrogen bridges.

Preferred neutral polar residues are selected from asparagine, cysteine, glutamine, serine, threonine, tyrosine, citrulline, N-methylserine, homoserine, allo-threonine and 3,5-dinitro-tyrosine and β-homoserine, The residues having a non-polar, hydrophobic side chain are residues that are uncharged under physiological conditions, preferably with a hydropathy index above 0, particularly preferably above 3. Preferred non-polar, hydrophobic side chains are selected from alkyl, alkylene, alkoxy, alkenoxy, alkylsulfanyl and alkenylsulfanyl residues having from 1 to 10, preferably from 2 to 6, carbon atoms, or aryl residues having from 5 to 12 carbon atoms. Preferred residues having a non-polar, hydrophobic side chain are selected from leucine, isoleucine, valine, methionine, alanine, phenylalanine, N-methylleucine, tert-butylglycine, cyclohexylalanine, β-alanine, 1-aminocyclohexylcarboxylic acid, N-methylisoleucine, norleucine, norvaline and N-methylvaline.

'Under physiological conditions' is to be understood as meaning a pH of from 6 to 8 and a temperature of from 30° C. to 40° C., preferably a temperature of 37° C., a pH of 7.4 and an osmotic pressure of 300 mosmol/kg.

NT is the free N-terminus of $X_1$ or a modified N-terminal amino group. CT is the free C-terminal carboxyl group of the C-terminal amino acid (—COOH) or a modified C-terminal carboxyl group. "Modified N-terminal amino group" and "modified C-terminal carboxyl group" means that the amino group or carboxyl group has been altered (e.g. reduced or substituted).

NT accordingly represents the free N-terminus of the amino acid $X_1$ or a modification of the N-terminal amino group (which replaces the N-terminal amino group of the amino acid $X_1$ by NT) having the general formula $NR_1R_2$. $NT=NR_1R_2$, wherein $R_1$ and $R_2$ are independent of one another and are preferably selected from hydrogen or from the following groups:

(i) a straight-chain, branched, cyclic or heterocyclic alkyl group, such as, for example, methyl, ethyl, n-propyl, isopropyl, n-butyl, isobutyl or cyclohexyl;

(ii) a straight-chain, branched, cyclic or heterocyclic alkanoyl group, such as, for example, acetyl or methanoyl (formyl), propionyl, n-butyryl, isobutyryl, pentanoyl, hexanoyl or cyclohexanoyl;

(iii) a reporter group, preferably a fluorescent dye (such as e.g. fluorescein, Alexa488) or biotin;

(iv) together with $COR_3$ (see below) a linker between the N- and C-terminus in order to obtain a cyclic peptide, for example based on guanidine, ethylene glycol oligomers, 2,4-diaminobutyric acid, 2,3-diaminopropionic acid, 2,2'-diaminopimelic acid, desmosine or isodesmosine.

(v) a linker for the coupling of a further peptide or peptide derivative ($Y_1$) via a specific chemical or enzymatic reaction, for example based on iodo-, bromo- or chloroalkanoic acids (e.g. iodoacetic acid) or maleimide for coupling to a thiol-containing peptide, or also a different reactive group (e.g. amino group, thiol group) for the coupling of a second peptide or peptide derivative (e.g. as active ester, aldehyde or thioester) as carrier protein.

(vi) a linker as mentioned in (v), to which a further peptide or peptide derivative $Y_1$ is coupled.

Examples of N-terminal modifications are acetylated formylated and preferably guanidated N-termini.

Preferably, a further peptide or peptide derivative Y, is coupled via NT. $Y_1$ is preferably a biopolymer (e.g. peptide) which introduces the antimicrobial peptide according to formula 1 into bacteria and thereby increases the activity of the antimicrobial peptide towards that bacterium and/or introduces it into mammalian cells and thereby permits the treatment of bacteria which are concealed in mammalian cells. Y, is linked via NT to $X_1$ of the peptide either permanently (e.g. peptide or amide bond for NT=$NH_2$ or thioether for NT=SH, iodoacetate or maleimide) or by a bond which is cleavable under certain conditions (such as e.g. disulfide bridges or acid-labile linkers). Preferred sequences for $Y_1$ are cell-penetrating peptides (CPP), for example penetratin, Tat peptides, model amphipathic peptides and transportans (Langel, U. in *Handbook of Cell-Penetrating Peptides* 5-28. CRC—Taylor & Francis Group, 2006).

A linker is a name for molecules or molecule groups which are used to link two substances, preferred linkers contain two reactive groups (such as e.g. iodoacetate, maleimide, imido- or NHS-ester or hydrazide), which are bonded by a molecule bridge (e.g. polyethylene glycol) having preferably from 10 to 20 carbon atoms.

CT is the free C-terminal carboxyl group of the C-terminal amino acid (—COOH) or a modified C-terminal carboxyl group, preferably having the general formula $COR_3$ ($R_3$ replaces the hydroxyl group of the last amino acid), $X_5$—$COR_3$ or $X_6$—$COR_3$ or $X_5X_6$—$COR_3$.

$COR_3$ is preferably selected from the following groups:
i. carboxyl ($R_3$ is a free hydroxyl group), an ester ($R_3$ is an alkoxy group), an amide ($R_3$ is an amine) or an imide;
ii. a linker which, together with NT, bridges the N- and C-termini to a cyclic peptide;
iii. $COR_3$, wherein $R_3$ is either an additional amino acid residue selected from the group comprising Pro, Ile, Leu, Arg and Gln, or wherein $R_3$ is a peptide having preferably from two to six amino acids, of which at least one amino acid is selected from the group comprising Pro, Ile, Leu, Arg and Gln, wherein this is substituted by a member from the group with carboxyl ($R_3$ is a free hydroxyl group), an ester ($R_3$ is an alcohol, such as methanol, ethanol, propanol, isopropanol or butanol), an amide ($R_3$ is an amide) or an imide ($R_3$ is an alkylamine or dialkylamine, such as methylamine, ethylamine, dimethylamine or cyclohexylamine).
iv. $COR_3$ wherein $R_3$ is an additional, branched amino acid, in order to form a dimeric or oligomeric structure, such as, for example, lysine, hydroxylysine, ornithine, 2,4-diaminobutyric acid, 2,3-diaminopropionic acid, 2,2'-diaminopimelic acid, desmosine, isodesmosine or a combination of these branched amino acids.
v. a linker for the coupling of a further peptide or peptide derivative ($Y_1$) via a specific chemical or enzymatic reaction, for example based on iodo-, bromo- or chloro-alkanoic acids (e.g. iodoacetic acid) or maleimide for coupling to a thiol-containing peptide or also another reactive group (e.g. amino group, thiol group) for the coupling of a second peptide or peptide derivative (e.g. as active ester, aldehyde or thioester) as carrier protein.
vi. a linker as mentioned in (v), to which a further peptide or peptide derivative $Y_1$ is coupled.

In this manner, C-terminal peptide derivatives can be obtained as ester ($R_3$=alkoxy), amide ($R_3$=amine, e.g. —$NH_2$ or imine, e.g. —$NHC_3H_7$) or imide or a peptide that has been lengthened by further amino acids selected from the group containing Pro, Ile, Arg and Val and have likewise again been modified at the C-terminus as ester, amide or imide. Further peptide derivatives can be formed by modifications of the N-terminal or C-terminal ends of the peptides. These changes can be, for example, an additional alkyl or alkanoyl group (either with a straight chain or branched, cyclic or heterocyclic) or an additional guanidino group or an additional macromolecule or a reporter residue, which is linked either permanently or by a compound that is cleavable under certain conditions (such as disulfide bridges or acid-labile linkers).

A modification of the C-terminus preferably takes place by means of thioester synthesis and subsequent substitution with primary amines.

All the natural amino acids, non-natural amino acids or amino acid derivatives (such as e.g. imino acids) which form the peptides or peptide derivatives according to the invention can be present in either the L- or D-conformation. Unless specified otherwise, the structural units in the sequences are, however, preferably in the L-conformation.

The modifications of the N- and C-termini allow the peptides to be coupled to other groups, such as, for example, other amino acid sequences (multimeric peptides or proteins optionally being created thereby) or other biomolecules which have the function of a carrier or label, for example of $Y_1$ via NT. In a specific embodiment, the molecule functions as a carrier for combating the bacterial infection in mammalian cells or transporting the antibacterial peptide and peptide derivative into bacteria into which the antibacterial peptide cannot penetrate on its own (e.g. gram-positive bacteria). Examples of such cell-penetrating peptides (CPP) are, for example, penetratins, Tat peptides, model amphipathic peptides and transportans. In addition, the site of the infection can be recognised by the coupled structure (target molecule) and the antibiotic substance can thereby be brought into the vicinity of the (bacterial) cell in order to combat it. Such target molecules are, for example, molecules that are known to bind to lipopolysaccharide (LPS) molecules, which form the outside of the gram-negative bacteria. Known compounds for this application are, for example, anchor peptides, such as the AcmA motif from Lactobacillus or an antibody directed against lipopolysaccharide. The latter variant is preferred because it also has an intrinsic antibiotic effect and can therefore be used to increase the activity of the peptides according to the invention.

By the coupling of a cell-penetrating peptide sequence, such as penetratin, it is possible on the one hand to increase the activity towards gram-negative and gram-positive bacteria, or to extend the spectrum of action to other gram-positive and gram-negative bacteria, and on the other hand to introduce the antimicrobial peptides into mammalian cells, so that bacteria, fungi or viruses concealed in those cells can also be reached. The coupling of penetratin via a thioether bridge forms part of the invention. The C-terminus of the penetratin was thereby lengthened by a cysteine and coupled to the antimicrobial peptide labelled at the N-terminus with iodoacetic acid.

The term "peptide" as used here denotes a sequence of amino acids which are linked via a peptide bond, wherein the amino acids are preferably selected from the twenty proteinogenic amino acids and wherein the amino acids can be present in the L-configuration or D-configuration, or in the case of isoleucine and threonine also in the D-allo-configuration (only inversion of one of the two chiral centres). Also included are peptides which have been altered by substitutions and/or modifications of one or more amino acid residues by chemical groups, those chemical groups being other than the natural protein-forming amino acid residues, such as, for example, non-proteinogenic α-amino acids, β-amino acids or peptide having an altered backbone. The expression "altered backbone" means that at least one peptide bond has been chemically modified, that is to say replaced by a bond that is not cleavable under physiological conditions and cannot be cut by endoproteases.

The non-cleavable bond is preferably a modified peptide bond such as, for example, a reduced peptide bond, an alkylated amide bond or a thioamide bond. A reduced amide bond is a peptide bond in which the carbonyl group (C=O) has been reduced to a hydroxyl group (HCOH) or a methylene group ($CH_2$). An alkylated amide bond is a peptide bond alkylated at either the nitrogen (N-alpha) or carbon atom (C-alpha). The alkyl residue has preferably from 1 to 3 carbon atoms. An example is N-methylation.

The expression 'altered backbone' additionally includes other groups which are suitable for forming a covalent bond both with the COOH group of the preceding amino acid residue and with the $NH_2$ group of the following amino acid residue, and which therefore do not necessarily maintain the peptide backbone structure, such as, for example, sugar amino acid dipeptide isosters, azapeptides, 6-homopolymers, gamma-peptides, depsipeptides (ester bridges in the backbone), Y-lactam analogs, oligo(phenyleneethylene)s, vinylogous sulfone peptides, poly-N-substituted glycines or oligocarbamates. Modifications of the backbone are preferred at positions that are susceptible to enzymatic degradation, particularly at the six C-terminal residues of the peptides according to formulae 4 to 9 (oncocin or oncopeltus peptide derivatives), particularly preferably positions 14 to 19, $R\text{-}X_3\text{-}I_{16}\text{-}Y_{17}\text{-}N_{15}\text{-}X_4$). Therefore, preferably at least one of the bonds between $X_3\text{-}I_{15}$ (e.g. Arg-Ile), $N_{15}\text{-}X_4$ (e.g. Asn-Arg), $X_4\text{-}NH_2$ (e.g. $Arg\text{-}NH_2$), $X_6\text{-}X_7$ (e.g. Arg-Leu or Arg-Ile) is a bond that is not cleavable for proteases. This non-cleavable bond is preferably selected from the group of the reduced amide bonds, alkylated amide bonds or thioamide bonds.

The peptides according to the invention are preferably linear. Alternatively, the peptides, in particular the apidaecin derivatives, are also cyclic, that is to say preferably the first (N-terminus) and the last amino acid (C-terminus) are linked via a peptide bond or a linker. However, cyclisations between a side chain (e.g. lysine) and the C-terminus, a side chain (e.g. glutamic acid or aspartic acid) and the N-terminus or between two side chains (e.g. lysine and glutamic acid or aspartic acid) are also included.

Methods for the preparation of the above-mentioned novel compounds having antibiotic activity also form part of this invention.

The peptides or peptide derivatives of this invention can be prepared either synthetically or, where applicable, recombinantly by conventional methods. Preferably, the peptides or peptide derivatives of this invention are prepared conventionally using the known synthesis techniques, as described, for example, by Merrifield. Alternatively, the peptides described in this invention are prepared by recombinant techniques, by cloning a DNA fragment which contains a nucleic acid sequence that codes for one of the above-described peptides and expressing it, for example, in a microorganism or a host cell. The coding nucleic acid sequences can be prepared synthetically or obtained by side-specific mutagenesis of an existing nucleic acid sequence (e.g. sequence coding for the wild-type oncopeltus 4). The coding sequence so prepared can be amplified by RNA (or DNA) with correspondingly prepared primers in a polymerase chain reaction (PCR) by known techniques. After purification, for example by means of agarose gel electrophoresis, the PCR product is ligated into a vector and the host cell is finally transformed with the corresponding recombinant plasmid. Recombinant techniques are known for various host cells, for example *E. coli, Bacillus, Lactobacillus, Streptomyces*, mammalian cells (e.g. CHO (Chinese hamster ovary) or COS-1 cells), yeast cells (e.g. *Saccharomyces, Schizophyllum*), insect cells or viral expression systems (e.g. baculovirus system). After conventional recombinant preparation, the peptides of this invention can be isolated from the host cells, either by conventional cell disruption techniques or from the cell medium by conventional methods, for example liquid chromatography, in particular affinity chromatography. The antimicrobial peptide can be expressed as a single peptide or as an oligomer. The oligomers can thereby contain a plurality of peptide sequences, which are linked via the N- or C-terminus, or even contain an N- or C-terminal tag, which permits easier purification of the recombinant peptides or protein constructs. Conventional techniques of molecular biology and side-specific mutagenesis can be used to alter the sequence further and thus obtain the desired non-native peptide sequences. These recombinant techniques have already been used for many antimicrobial peptides including apidaecin (see e.g. Maeno M et al. 1993. Biosci Biotechnol Biochem 57:1206-7).

It is also possible to introduce amino acids that do not occur naturally into the peptides by genetic engineering (Noren C at al. 1989. Science 244: 182-8; Ellman J et al. 1991 Methods Enzymol. 202: 301-36).

The peptides can then be isolated from the host cell culture or the in vitro translation system. This can be achieved using the conventional techniques for protein purification and isolation, which are known from the prior art. Such techniques can include, for example, immunoadsorption or affinity chromatography. It is additionally possible to provide the peptides with a tag (e.g. histidine tag) during the synthesis, which permits rapid binding and purification. The tag can subsequently be cleaved enzymatically in order to obtain the active peptide sequence.

If the peptide itself cannot be coded or expressed but is very similar to a codable or expressible peptide, the method can first be applied to the similar peptide, in order subsequently to convert it chemically or enzymatically in one or more steps into the desired peptide or peptidomimetic.

The modified peptides according to the invention can be used individually, in combination, as multimers or as branched multimers. Expedient combinations of the peptides according to the invention include concatamers, in which the peptides according to the invention are linked with one another sequentially or via spacers, for example in the form of a peptide dimer or a peptide trimer etc., by the individual peptides being strung together. This multimer can be composed of peptides or peptide derivatives having identical sequences or different sequences according to formula 1.

The modified peptides can additionally be coupled to a biocompatible protein, for example human serum albumin, humanised antibodies, liposomes, micelles, synthetic polymers, nanoparticles and phages. Alternatively, multimers, in which the peptides or peptide derivatives according to the invention are combined individually, can be prepared in the form of dendrimers or clusters, wherein three or more peptides are bonded to one centre.

In one embodiment, a plurality of peptides can be prepared as multimeric constructs or arrangement. Thus, for example, optional amino acids (e.g. Gly-Ser-) or other spacers based on amino acids or other chemical compounds can be attached to the N- or C-terminus in order to link two or more peptides with one another or couple them to a carrier. This arrangement can take the form of one or more of the above-described synthetic peptides coupled to a carrier protein. Alternatively, an arrangement contains a plurality of peptides, each expressed as a multiple antigenic peptide, optionally coupled to a carrier protein. In a further variant, the selected peptides are linked sequentially and are expressed as recombinant protein or polypeptide. In one embodiment, a plurality of peptides are linked sequentially, with or without amino acids as spacers, in order to obtain a larger recombinant protein. Alternatively, the recombinant protein can be fused to a carrier protein.

In another embodiment, the multimeric constructs contain at least two peptides, wherein one peptide is coupled to the other peptide via any desired amino acid. Any desired number of further peptides can be attached to any desired further amino acids of these peptides. In a further embodiment of a multimeric arrangement which contains at least two peptides, the second peptide or the further peptides is/are coupled to a branched structure of the other peptides of the basic structure. Alternatively, each further peptide is linked covalently via the group NT or CT to another peptide of the arrangement.

In another embodiment of a multimeric construct or an arrangement having at least two peptides, at least one or more peptides are bonded to a carrier. In another embodiment, one or more of the mentioned peptides is/are a synthetic peptide fused to a carrier protein. Furthermore, there is the alternative of combining a plurality of the above-described peptides sequentially, with or without flanking sequences, to form a linear polypeptide. The peptides or the polypeptide are either coupled to the same carrier, or different peptides can be coupled individually as peptides to one or different immunologically inert carrier proteins.

Suitable carriers can improve the stability, the administration or the production, or can alter the activity spectrum of the peptides. Examples of carriers are human albumin, polyethylene glycol or other biopolymers or other naturally or non-naturally occurring polymers. In an embodiment, the main component is preferably a protein or other molecule which can increase the peptide stability. An experienced person can easily select a suitable coupling unit.

In yet another embodiment, the peptides are arranged in the form of a multiple antigenic peptide (MAP). This system uses a central unit of lysine residues onto which several copies of the same peptide according to the invention are synthesised. Each MAP contains several copies of one or more of the peptides according to the invention. One form of an MAP contains at least three but preferably four or more peptides. A person skilled in the art can easily prepare any desired number of multimeric compounds according to the peptides identified in the above formula. All such multimeric arrangements and constructs are to form part of this invention.

Further combinations in the form of multimers can be prepared at, the surface of particles, the peptides or peptidomimetics being presented on their surface. The particle can then function as a carrier of a peptide or peptidomimetic and can at the same time act as a detectable marker. Multimers can be obtained, for example, by N-terminal biotinylation of the N-terminal end of the peptide or peptidomimetic chains and subsequent complex formation with streptavidin. Because streptavidin is able to bind four biotin molecules or conjugates with high affinity, very stable tetrameric peptide complexes are obtained by this method. Multimers can be prepared from identical or different peptides or peptidomimetics according to the invention. Preferably, the multimers according to the invention contain two or more peptides or peptidomimetics, in which each component makes a certain contribution to the biocidal activity (target recognition, antimicrobial activity, purification).

This invention also provides the use of the peptides or peptide derivatives according to the invention in medicine or pharmacy, for example for therapy with an antibiotic or in a composition having antimicrobial (in particular bactericidal) activity.

The invention also provides the peptides modified according to the invention for use in medicine, as an antibiotic, in a disinfectant or cleaning agent, as a preservative or in a packaging material. The modified peptides according to the invention are particularly suitable for the treatment of microbial, bacterial or fungal infections.

The invention also provides the use of the peptides modified according to the invention for the preparation of a medicament, in particular of an antibiotic, in particular for the treatment of microbial infections, for example by bacteria, viruses and fungi.

This invention further provides pharmaceutical compositions which comprise one or more peptides modified according to the invention or multimeric constructs, independently of the presence of other pharmaceutically active compounds.

The use of the peptides according to the invention as a pharmaceutical agent and/or for the preparation of an active ingredient that can be used as an antibiotic also forms part of this invention.

The modified peptides can also be used individually in pharmaceutical products. Alternatively, one or more modified peptides, as described above, can be fused or conjugated to another compound in order to increase the pharmacokinetics or bioavailability without triggering an immune response. Any desired number of individual peptides or multimeric constructs can be mixed with one another in order to prepare an individual composition.

A pharmaceutical composition according to the invention comprises a therapeutically effective amount of one or more modified peptides of this invention. Once composed, the pharmaceutical composition according to the invention can be administered directly to the subject in order to treat microbial (in particular bacterial) infections. To that end, a therapeutically effective amount of a composition according to the invention is administered to the subject to be treated.

The compositions according to the invention are intended to treat infections of a mammal, including a human being, infected with bacteria or fungi. At least one or alternatively also a plurality of peptides or multimeric constructs according to the invention can be mixed with a pharmacologically acceptable carrier or other components to form a composition having antimicrobial (in particular antibacterial or fungicidal) activity. For the use of such a composition, the chosen peptide is preferably prepared synthetically or also recombinantly, as described above.

The direct administration of this composition is carried out locally or systemically, preferably orally, parenterally, intraperitoneally, intravenously, intramuscularly, pulmonally or interstitially into the tissue.

The pharmaceutical composition can comprise further suitable and pharmaceutically acceptable carriers, extenders or solvents and can be in the form of a capsule, tablet, pastille, dragée, pill, drop, suppository, powder, spray, vaccine, ointment, paste, cream, inhalant, patch, aerosol or the like. There can be used as pharmaceutically acceptable carriers solvents, extenders or other liquid binders such as dispersing or suspension aids, surface-active agents, isotonic active ingredients, thickeners or emulsifiers, preservatives, encapsulating agents, solid binders or glidants, according to what is most suitable for the particular dosage and at the same time compatible with the peptide, peptidomimetic (peptide derivative), peptide conjugate or peptidomimetic conjugate.

The pharmaceutical composition therefore preferably comprises a pharmaceutically acceptable carrier. The expression "pharmaceutically acceptable carrier" in this case also includes a carrier for administration of the therapeutic composition, such as, for example, antibodies or polypeptides, genes or other therapeutic agents. The expression relates to any desired pharmaceutical carrier which does not, itself trigger the production of antibodies, which could be harmful for the individual to whom the formulation has been administered, and which does not possess excessive toxicity. Suitable "pharmaceutically acceptable carriers" can be large, slowly degradable macromolecules, such as, for example, proteins, polysaccharides, polylactonic acids, polyglycolic acids, polymeric amino acids, amino acid copolymers and inactivated virus constituents. Such carriers are well known to the person skilled in the art.

Salts of the peptides or functionally equivalent compounds can be prepared by known methods, which typically means that the peptides, peptidomimetics, peptide conjugates or peptidomimetic conjugates are mixed with a pharmaceutically acceptable acid to form an acid salt or with a pharmaceutically acceptable base to form a basic salt. Whether an acid or a base is pharmaceutically acceptable can easily be determined by a person skilled in the art with knowledge of the application and the formulation. Thus, for example, not all acids and bases that are acceptable for ex vivo applications can also be transferred to therapeutic formulations. Depending on the particular application, pharmaceutically acceptable acids can be both organic and inorganic in nature, for example formic acid, acetic acid, propionic acid, lactic acid, glycolic acid, oxalic acid, pyruvic acid, succinic acid, maleic acid, malonic acid, cinnamic acid, sulfuric acid, hydrochloric acid, hydrobromic acid, nitric acid, perchloric acid, phosphoric acid and thiocyanic acid, which form ammonium salts with the free amino groups of peptides and functionally equivalent compounds. Pharmaceutically acceptable bases, which form carboxylates with the free carboxylic acid groups of the peptides and functionally equivalent compounds, include ethylamine, methylamine, dimethylamine, triethylamine, isopropylamine, diisopropylamine and other mono-, di- and tri-alkylamines, as well as arylamines. Pharmaceutically acceptable solvents are also included.

Pharmaceutically acceptable salts can be used therein, such as, for example, salts of mineral acids, such as hydrochlorides, hydrobromides, phosphates, sulfates and the like; but also salts of organic acids, such as acetates, propionates, malonates, benzoates and the like. A comprehensive discussion of pharmaceutically acceptable ingredients will be found in Remington's Pharmaceutical Sciences (Mack Pub. Co., N.J., 1991).

Pharmaceutically acceptable carriers in the therapeutic compositions can contain liquids, for example water, salt water, glycerol and ethanol. In addition, auxiliary substances can be added, such as humectants or emulsifiers, pH-buffering substances and similar compounds can be present in such agents. Typically, the therapeutic compositions are prepared either in liquid form or as a suspension for injection, solid forms for dissolution or suspension in carrier liquids prior to injection are likewise possible. Liposomes are also included in the definition of a "pharmaceutically acceptable carrier".

For therapeutic treatment, modified peptides or peptide conjugates, as described above, can be produced and administered to a subject requiring them. The peptide or peptide conjugate can be administered to a subject in any desired suitable form, preferably in the form of a pharmaceutical composition which is adapted to the dosage form and is present in a dose appropriate for the desired treatment.

The pharmaceutical compositions of this invention can comprise further active compounds, for example conventional antibiotics (e.g. vancomycin, streptomycin, tetracycline, penicillin) or other antimicrobially active compounds, such as fungicides, for example intraconazole or myconazole. Other compounds which alleviate the symptoms associated with the infection, such as fever (salicylic acid) or skin eruption, can also be added.

In addition to the therapeutic use for the treatment of infections, or also in biological warfare, it is further possible to use the peptides or peptide derivatives according to the invention in disinfectants or cleaning agents (e.g. a bactericidal composition) which can be used for the disinfection or cleaning of surfaces or objects. Another field of application is packaging, where peptides can be bound to packaging material or incorporated therein, or as preservatives for other materials which can readily be degraded by microorganisms. The peptides or peptide derivatives according to the invention are suitable in particular for the packaging of foodstuffs, because they are not toxic either on contact or on ingestion.

A method for treating mammals infected with microbes (in particular bacteria or fungi), including the administration of an effective, therapeutically effective amount of the pharmaceutically active composition according to the invention, forms another part of this invention.

The expression "therapeutically effective amount" used here denotes the amount of a therapeutic agent, that is to say of a peptide, peptidomimetic, peptide conjugate or peptidomimetic conjugate according to the invention, which is capable of reducing or completely preventing the multiplication and colony formation of the bacteria or of achieving measurable therapeutic or prophylactic success. The effect can be determined, for example, for biopsies in culture, by testing the antibacterial activity or by another suitable method for assessing the extent and degree of a bacterial infection. The exact effective amount for a subject depends on its size and state of health, on the nature and extent of the disease and on the therapeutic agents or the combination of several therapeutic agents chosen for the treatment. The compositions according to the invention can be used in particular for reducing or preventing bacterial infections and/or biological or associated physical symptoms (e.g. fever). Methods of determining the initial dose by a doctor are known from the prior art. The doses determined must be safe and successful.

The amount of a protein, peptide or nucleic acid according to the invention that is necessary for an antibacterially effective dose can be determined in consideration of the pathogen that causes the infection, the severity of the infection, as well as the age, weight, gender, general physical condition etc. of the patient. The necessary amount of the active component, in order to be antibacterially and antimycotically effective without notable side-effects, depends on the pharmaceutical formulation used and the possible presence of further constituents such as antibiotics, antimycotics, etc. For the fields of use according to the invention, an effective dose can be between 0.01 nmol/kg and 50 nmol/kg, preferably between 0.2 nmol/ kg and 10 nmol/kg of the peptide, peptidomimetic, peptide conjugate or peptidomimetic conjugate in the treated individual.

Initial doses of the peptides, peptidomimetics, multimers, peptide conjugates or peptidomimetic conjugates according to the invention can optionally be followed by repeated administration. The frequency of the doses depends on the factors identified above and is preferably between one and six doses per day over a treatment period of approximately from three days to not more than one week.

In a further embodiment, the compounds are administered pulmonally in a specific amount, for example by an inhaler, atomiser, aerosol spray or a dry powder inhaler. Suitable formulations can be prepared by known methods and techniques. Transdermal or rectal application, as well as administration into the eye, may in some cases be appropriate.

It can be advantageous to administer the substances according to the invention more effectively by advanced forms of drug delivery (advanced drug delivery or targeting methods). Thus, if the digestive tract is to be avoided, the dosage form can comprise any desired substance or mixture that increases the bioavailability. This can be achieved, for example, by reducing the degradation, for example by an enzyme inhibitor or an antioxidant. It is better if the bioavailability of the compound is achieved by increasing the permeability of the absorption barrier, in most cases the mucosa. Substances that facilitate penetration can act in this manner; some increase the fluidity of the mucosa while others widen the interstices between the mucosal cells. Yet others reduce the viscosity of the mucous on the mucosa. The preferred uptake accelerators include amphiphilic substances such as cholic acid derivatives, phospholipids, ethanol, fatty acids, oleic acid, fatty acid derivatives, EDTA, carbomers, polycarbophil and chitosan.

Indications for which the modified peptides according to the invention, their conjugates or multimers can be used are bacterial infections with both gram-positive and gram-negative bacteria, for example *Escherichia coli, Enterobacter cloacae, Erwinia amylovora, Klebsiella pneumoniae, Morganella morganii, Pseudomonas aeruginosa, Salmonella typhimurium, Salmonella typhi, Shigella dysenteriae, Yersinia enterocolitica, Acinetobacter calcoaceticus, Agrobacterium tumefaciens, Francisella tularensis, Legionella pneumophila, Pseudomonas syringae, Rhizobium meliloti, Haemophilus influenzae.*

BRIEF DESCRIPTION OF THE DRAWINGS

The invention is explained below by the following exemplary embodiments and figures, without limiting the invention thereto.

DESCRIPTION OF PREFERRED EMBODIMENTS

Example 1

Peptide Synthesis and Modification

Figure 1:
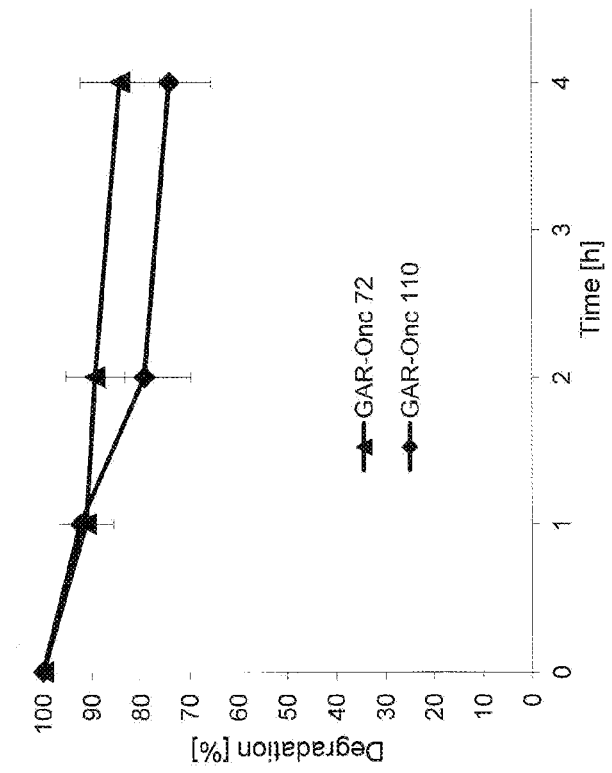
FIG. 1 shows the serum stability of Api 300 (SG), Api 301 (SG) (left), Onc 72 and Onc110 (right) in mouse serum (100%). The respective starting products (solid line) and the degradation products (broken line), where detected, are shown.
Figure 1:
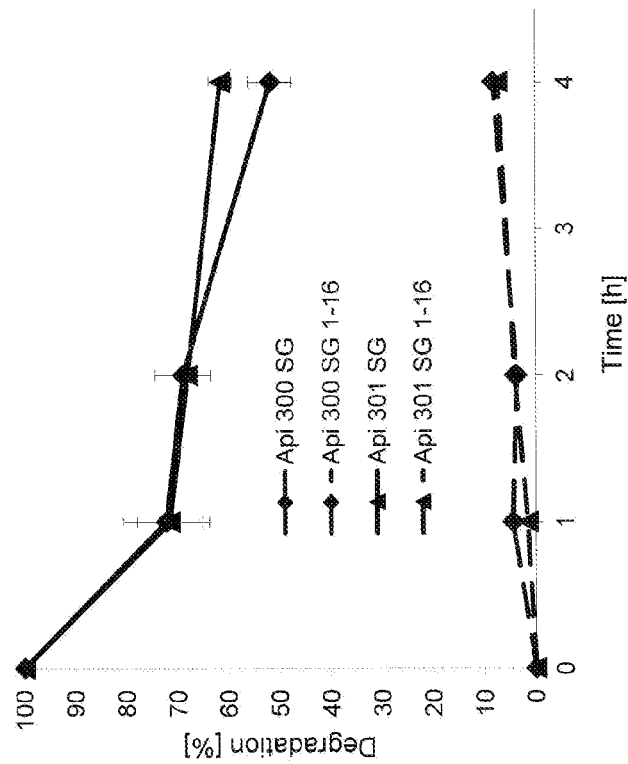
Figure 2:
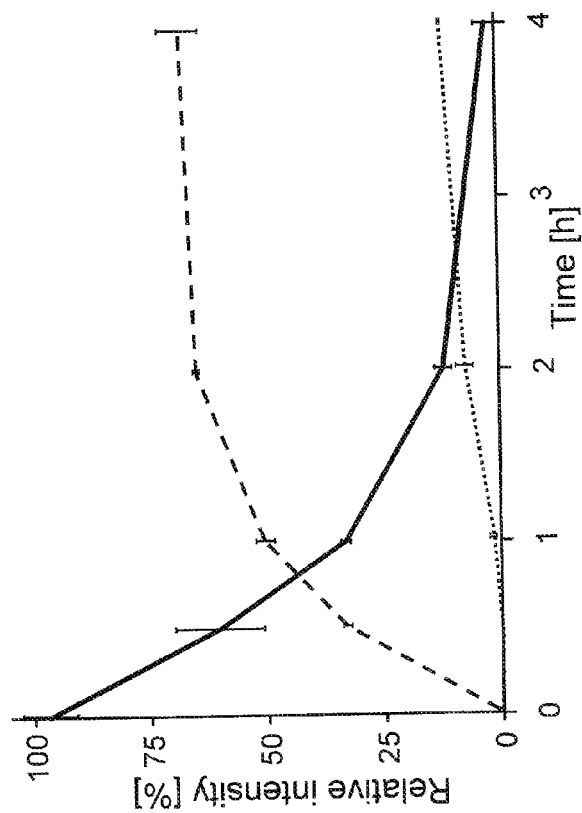
FIG. 2 shows the serum stability of Api 137 (sPEG$^{750}$-GRSG) (left, solid line) (SEQ ID NO. 21) and Api 137 (sPEG$^{750}$-GARSG) (right, solid line) (SEQ ID NO. 22) in 25% aqueous mouse serum (100%). The active ingredient released Api 137 (SG) (broken line) (SEQ ID NO. 18) und and the resulting degradation product, shortened at the C-terminus, Api 137 (SG) 1-16 (dotted line).
Figure 2:
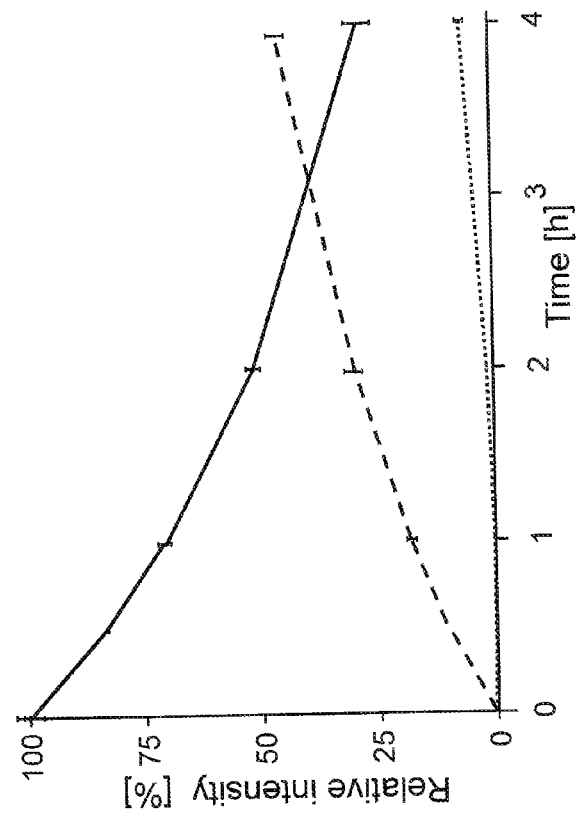
Figure 3:
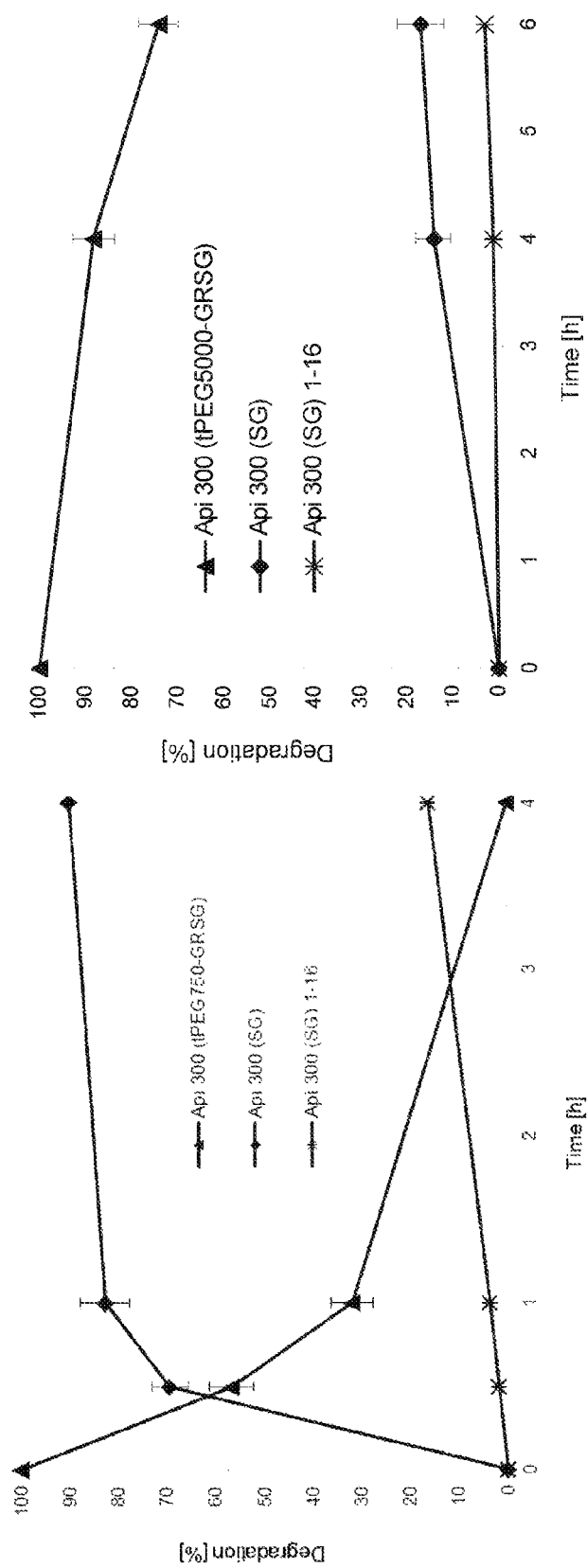
FIG. 3 shows the serum stability of Api 300 (tPEG$^{750}$-GRSG) (left) (SEQ ID NO. 32) and Api 300 (tPEG$^{5000}$-GRSG) (right) (SEQ ID NO. 35) in mouse serum (100%). The respective starting products (triangle), the active ingredient released Api 300 (SG) (lozenge) (SEQ ID NO. 25) and its degradation product shortened at the C-terminus Api300 (SG) 1-16 (asterisk) are shown.
Figure 4:
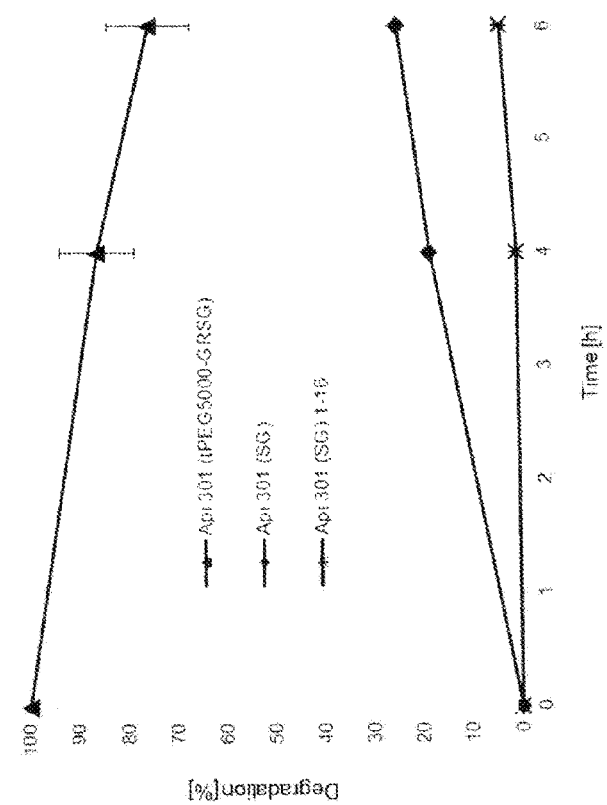
FIG. 4 shows the serum stability of Api 301 (tPEG$^{750}$-GRSG) (left) (SEQ ID NO. 45) and Api 301 (tPEG$^{5000}$-GRSG) (right) (SEQ ID NO. 48) in mouse serum (100%). The respective starting products (triangle), the active ingredient released Api 301 (SG) (lozenge) (SEQ ID NO. 38) and its degradation product shortened at the C-terminus Api301 (SG) 1-16 (asterisk) are shown.
Figure 4:
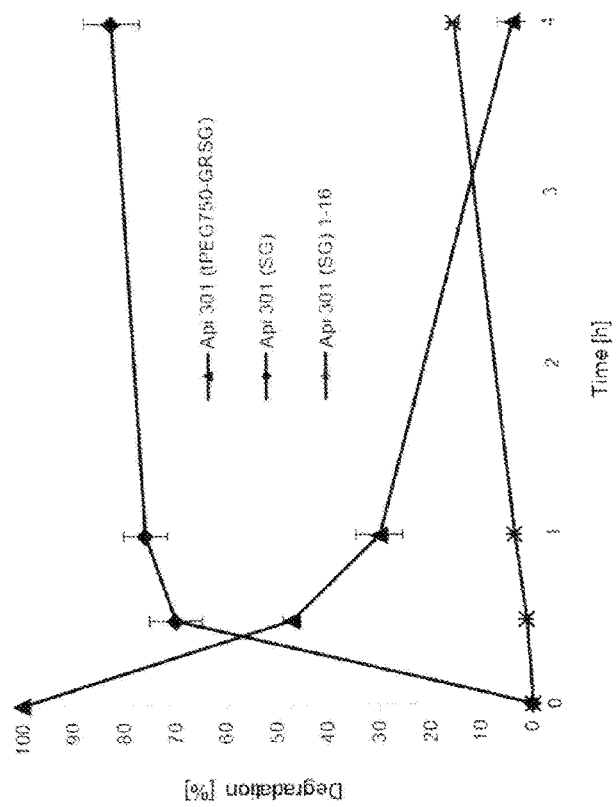
Figure 5:
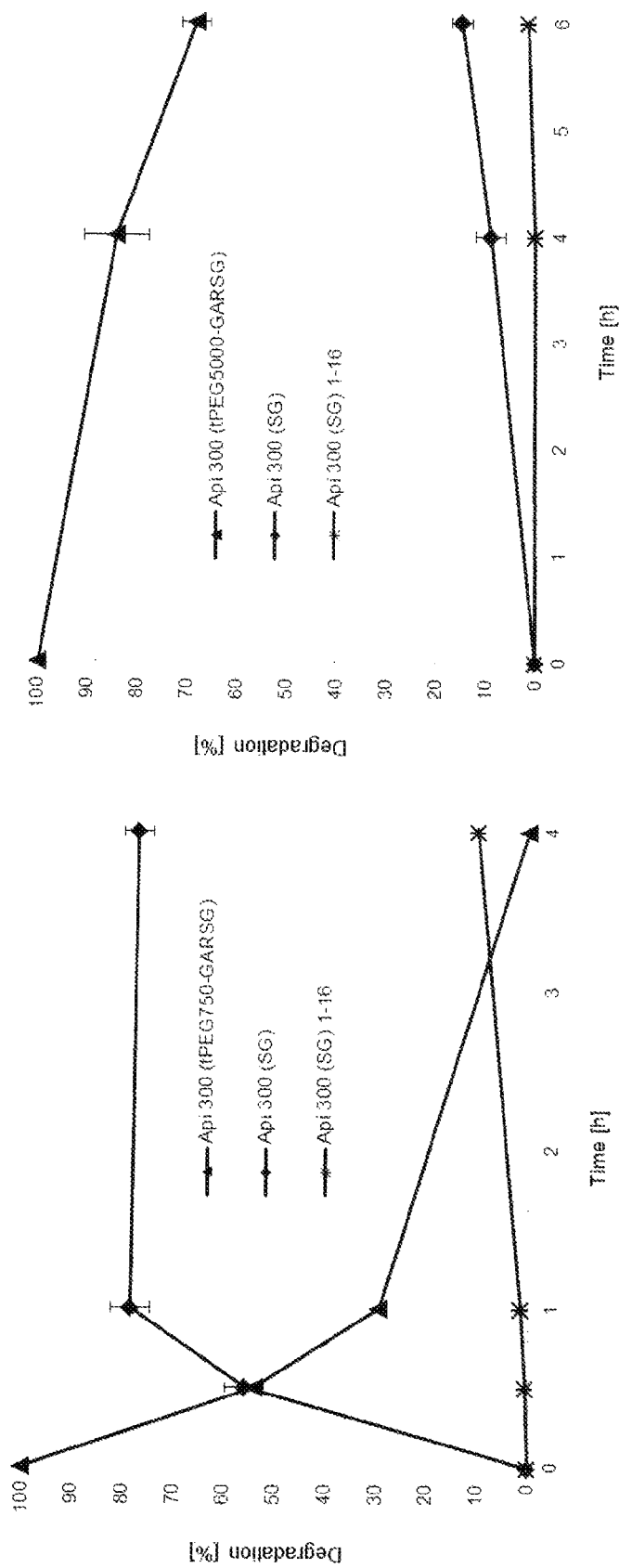
FIG. 5 shows the serum stability of Api 300 (tPEG$^{750}$-GARSG) (left) (SEQ ID NO. 33) and Api 300 (tPEG$^{5000}$-GARSG) (right) (SEQ ID NO. 36) in mouse serum (100%). The respective starting products (triangle), the active ingredient released Api 300 (SG) (lozenge) (SEQ ID NO. 25) and its degradation product shortened at the C-terminus Api300 (SG) 1-16 (asterisk) are shown.
Figure 6:
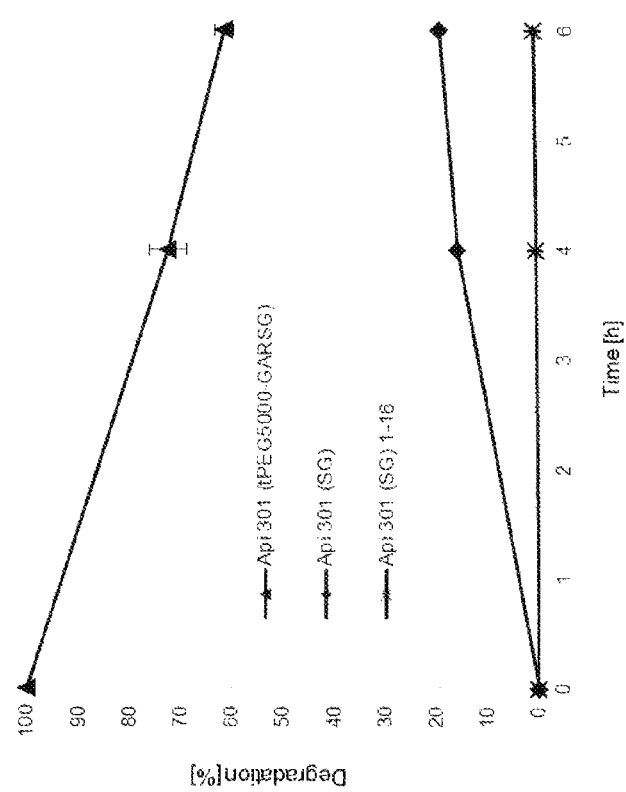
FIG. 6 shows the serum stability of Api 301 (tPEG$^{750}$-GARSG) (left) (SEQ ID NO. 46) and Api 301 (tPEG$^{5000}$-GARSG) (right) (SEQ ID NO. 49) in mouse serum (100%). The respective starting products (triangle), the active ingredient released Api 301 (SG) (lozenge) (SEQ ID NO. 38) and its degradation product shortened at the C-terminus Api301 (SG) 1-16 (asterisk) are shown.
Figure 6:
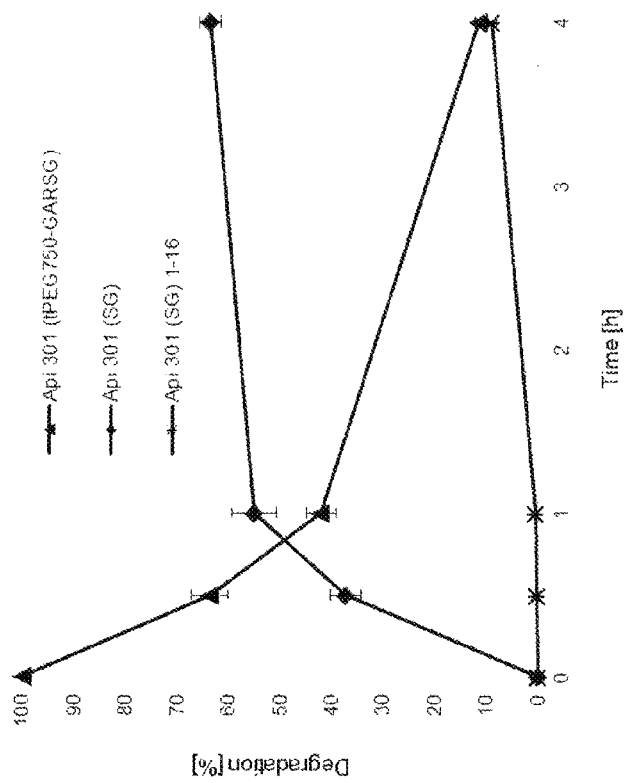
Figure 7:
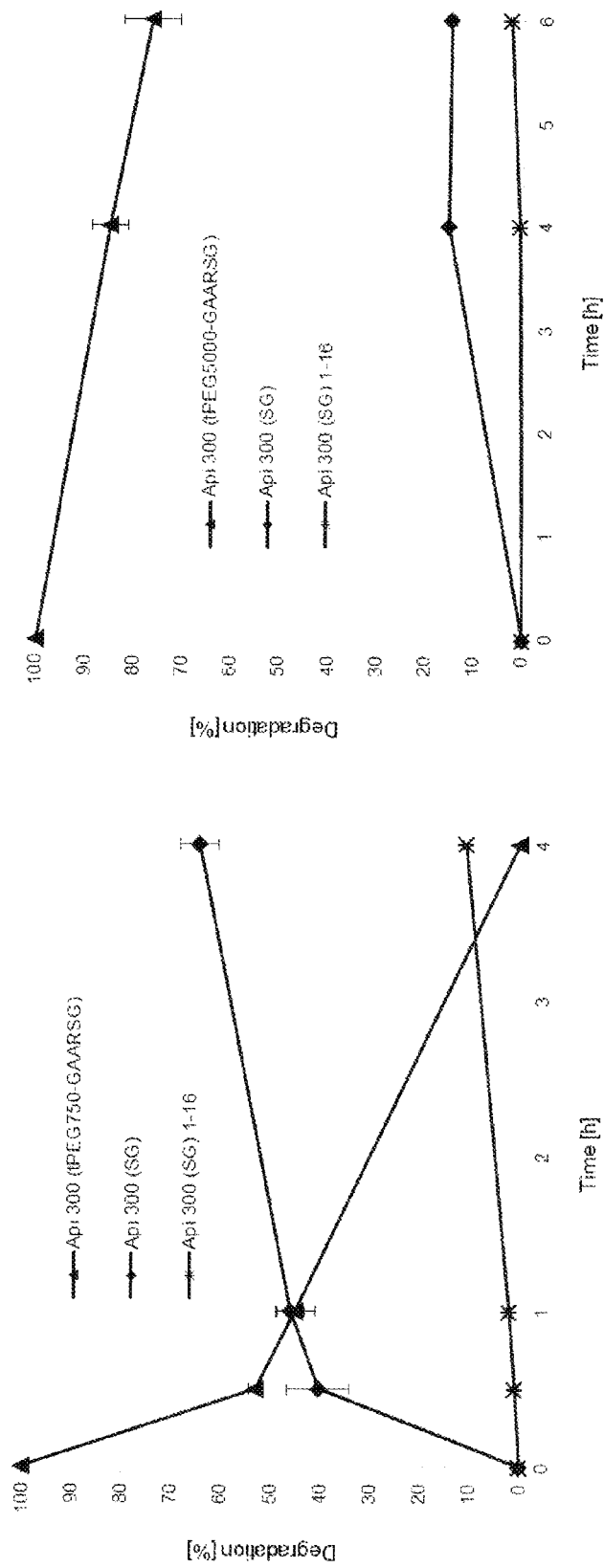
FIG. 7 shows the serum stability of Api 300 (tPEG$^{750}$-GAARSG) (left) (SEQ ID NO. 34) and Api 300 (tPEG$^{5000}$-GAARSG) (right) (SEQ ID NO. 37) in mouse serum (100%). The respective starting products (triangle), the active ingredient released Api 300 (SG) (lozenge) (SEQ ID NO. 25) and its degradation product shortened at the C-terminus Api300 (SG) 1-16 (asterisk) are shown.
Figure 8:
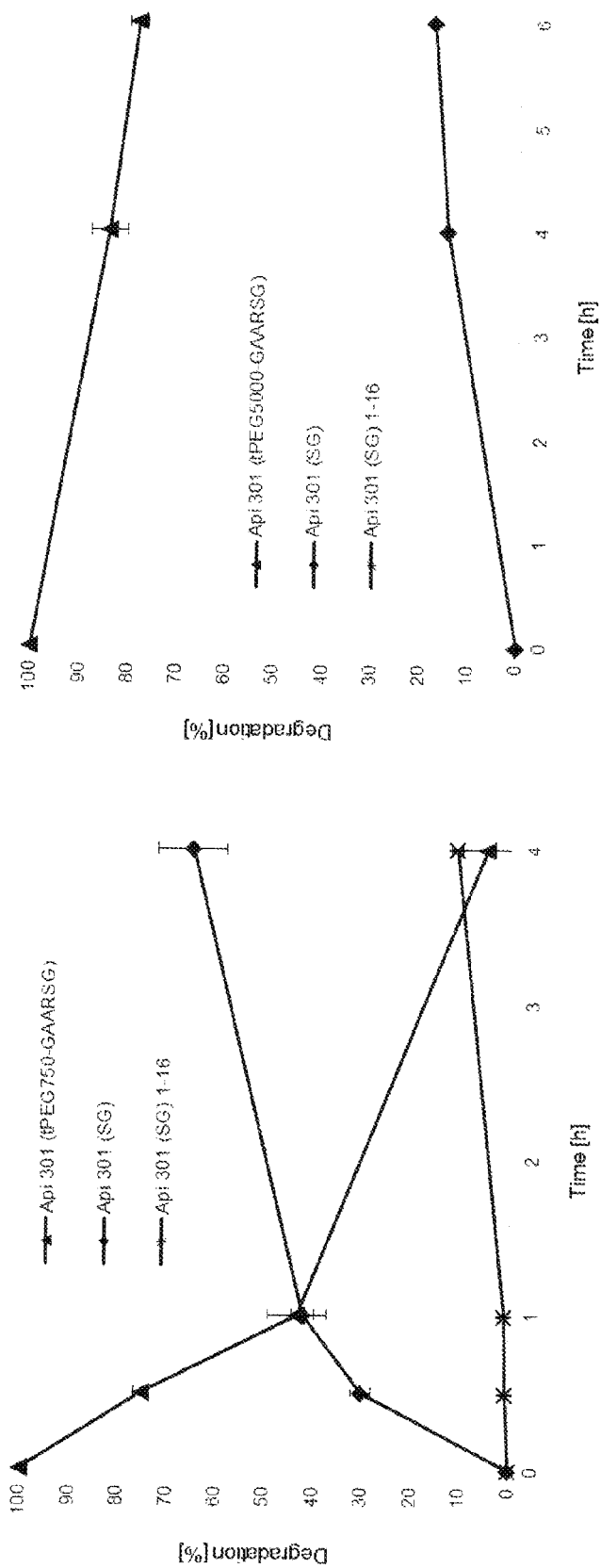
FIG. 8 shows the serum stability of Api 301 (tPEG$^{750}$-GAARSG) (left) (SEQ ID NO. 47) and Api 301 (tPEG$^{5000}$-GAARSG) (right) (SEQ ID NO. 50) in mouse serum (100%). The respective starting products (triangle), the active ingredient released Api 301 (SG) (lozenge) (SEQ ID NO. 37) and its degradation product shortened at the C-terminus Api301 (SG) 1-16 (asterisk) are shown.
Figure 9:
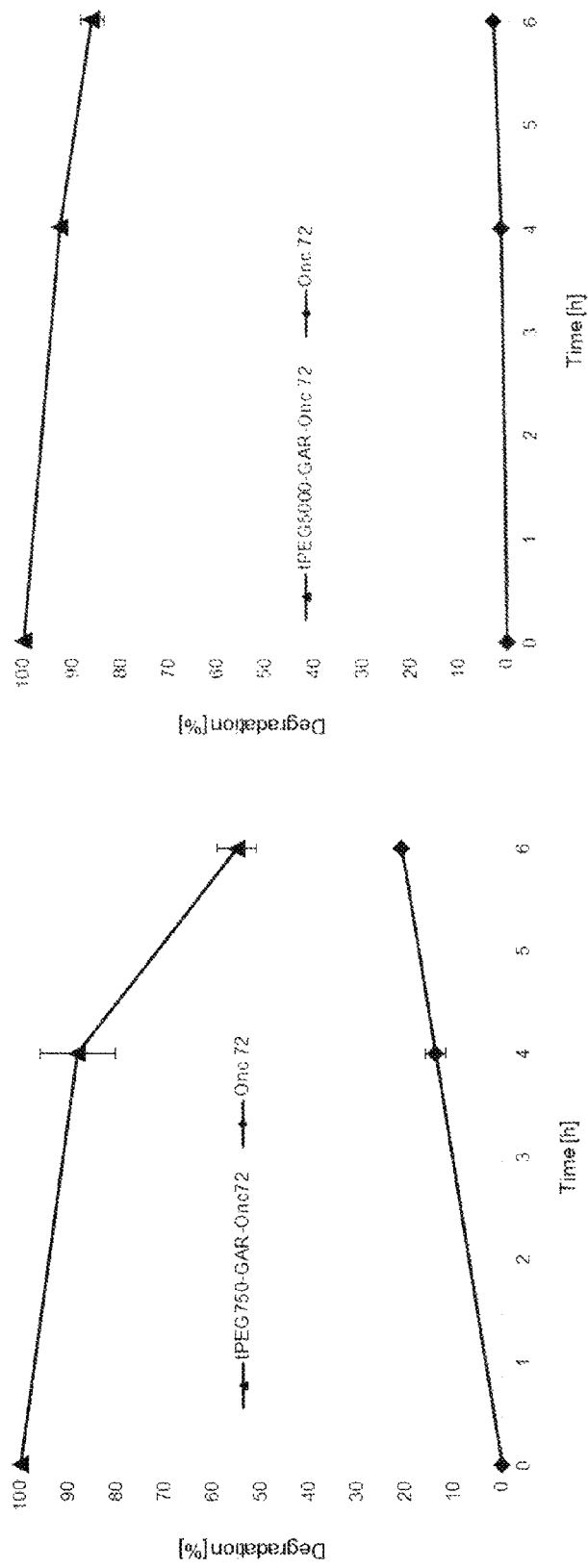
FIG. 9 shows the serum stability of tPEG$^{750}$-GAR-Onc 72 (left) and tPEG$^{5000}$-GAR-Onc 72 (right) in mouse serum (100%). The respective starting products (triangle) and the active ingredient released Onc72 (lozenge) are shown. Degradation products of Onc72 were not detected.
Figure 10:
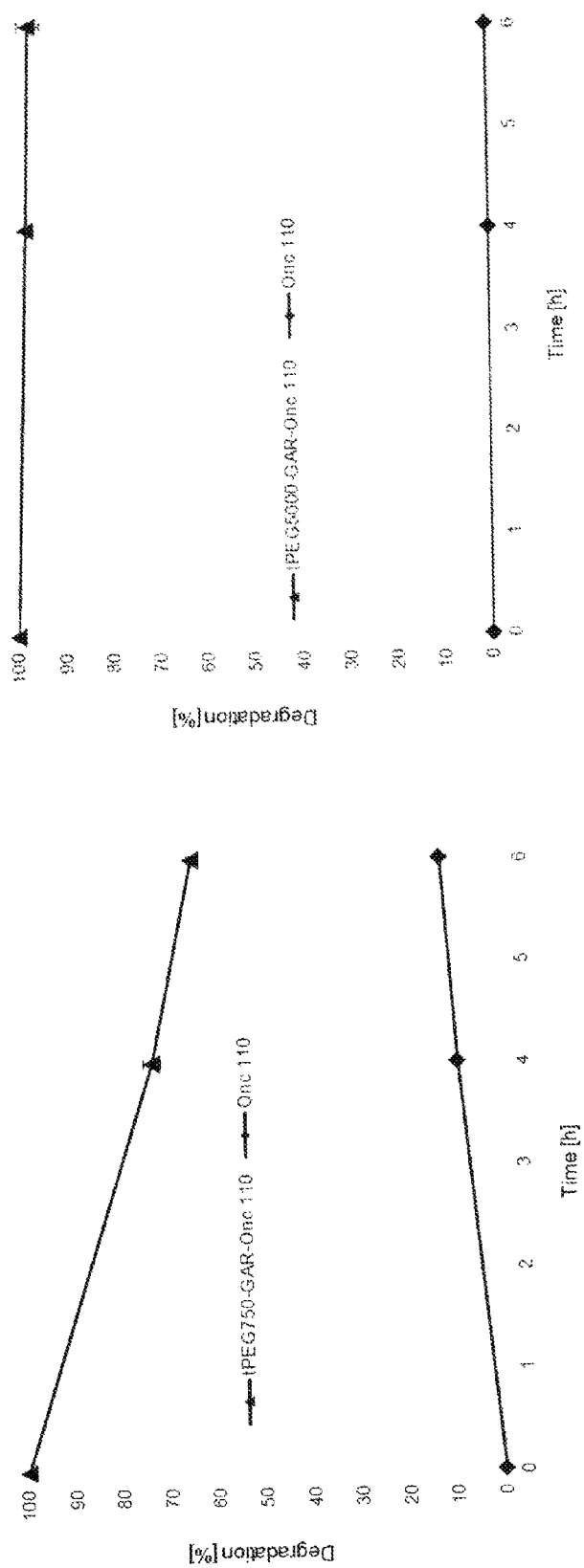
FIG. 10 shows the serum stability of tPEG$^{750}$-GAR-Onc 110 (left) and tPEG$^{5000}$-GAR-Onc 110 (right) in mouse serum (100%). The respective starting products (triangle) and the active ingredient released Onc 110 (lozenge) are shown. Degradation products of Onc 110 were not detected.

1. Peptide Synthesis:

All the chemicals for the peptide synthesis were obtained, unless otherwise indicated, from Fluka Chemie GmbH (Buchs, Switzerland) in the greatest possible purity.

The peptides were synthesised by means of conventional solid-phase peptide synthesis using the Fmoc/$^t$Bu strategy. All standard Fmoc amino acids were obtained from Multi-SynTech GmbH (Witten, Germany) or Orpegen Pharma GmbH (Heidelberg, Germany). Trans-4-hydroxyproline (t-4-Hyp) and tert-leucine were obtained from Novabiochem (Merck Biosciences GmbH, Darmstadt, Germany).

The peptides were synthesised on a 25 µmol scale with the aid of a SYRO 2000 peptide synthesis robot (MultiSynTech GmbH, Witten, Germany). To that end, 42 mg of Leu-Wang resin (load: 0.6 mmol/g) were weighed out per synthesis reactor and swollen for 30 minutes in DMF. After cleavage of the N-terminal Fmoc protecting group, the peptides were synthesised with the following synthesis cycle (Table 2).

TABLE 2

Synthesis cycle of the automatic multiple solid-phase peptide synthesis (SYRO 2000) for coupling of an amino acid.

| Synthesis step | Reagents | Reaction time |
|---|---|---|
| Amino acid coupling | 8 eq. amino acid in HOBt/DMF (0.5 mol/l) and DIC/DMF (2.0 mol/l) | 60 min |
| Washing | 3 × with 600 µl DMF each time | 1 min |
| Fmoc cleavage | 400 µl 40% piperidine/DMF | 3 min |
| | 500 µl 20% piperidine/DMF | 10 min |
| Washing | 6 × with 600 µl DMF each time | 1 min |

For synthesis on a 100 µmol scale with the aid of a Liberty microwave peptide synthesis robot (CEM GmbH, Kamp-Lintfort, Germany), 156.3 mg of commercially available Leu-Wang resin from NovaBiochem (load: 0.64 mmol/g) were weighed out per synthesis reactor and swollen for 30 minutes in DMF. After cleavage of the N-terminal Fmoc protecting group, the peptides were inter alia synthesised with the following synthesis cycle (Table 3).

TABLE 3

Synthesis cycle of the automatic multiple solid-phase synthesis (Liberty) for coupling of the individual amino acids.

| Cycle | Synthesis step | Reagents | Reaction time |
|---|---|---|---|
| Amino acid (0.10-single) | Washing | 7.0 ml DMF | 0.5 min |
| | Fmoc cleavage | 7.0 ml 20% piperidine 35 watts at 75° C. | |
| | Washing | 5.0 ml DMF | |
| | Fmoc cleavage | 7.0 ml 20% piperidine 35 watts at 75° C. | 3 min |
| | Washing | 4 × with 7.0 ml DMF each time | |
| | Coupling | 2.5 ml 0.2 mol/l amino acid in DMF 1.0 ml 0.5 mol/l HBTU 25 watts at 75° C. | 10 min |
| | Washing | 3 × with 7.0 ml DMF each time | |

The peptides were synthesised either as acid on Wang resin or Leu-Wang resin or as acid amide on Rink amide 4-methylbenzyihydrylarnine (MBNA) resin (0.67 mmol/g) from MultiSynTech GmbH (Witten, Germany).

There were used as side chain protecting groups triphenylmethyl (trityl) for Cys, Asn, His and Gln, tert-butyl ether ($^tBu$) for Tyr, Ser and Thr, tert-butyl ester ($O^tBu$) for Asp and Glu, ω-N-2,2,4,6,7-pentamethyldihydrobenzofuran-5-sulfonyl (Pbf) for Arg, tert-butyloxy-carbonyl (Boc) for Lys and Orn. The temporary Fmoc protecting group was cleaved with 40% piperidine (Biosolye BV, Valkenswaard, Netherlands) in DMF (v/v) for 5 minutes and again with fresh 20% piperidine in DMF (v/v) for 10 minutes.

2. Modification of the Peptides:

a.) Guanidation of the N-terminus:

The resin (1 eq.) was first swollen for 20 minutes in DMF. It was then incubated for 3 hours at room temperature and with shaking with HBTU in DMF (0.5 mol/l, 10 eq.) and NMM (10 eq.). The reaction solution was then renewed and the suspension was incubated for a further 4 hours. When the reaction was complete, the reaction solution was separated off and the resin was washed six times with DMF or DCM.

b.) Lodoacetylation

The resin (1 eq.) was first swollen for 20 minutes in DMF. Lodoacetic acid (8 eq.) and HOBt in DMF (0.5 mol/l, 8 eq.) were then added, and the reaction was activated with DIC (8 eq.). The reaction mixture was then incubated for 16 hours at room temperature in the dark and with shaking. When the reaction was complete, the reaction solution was separated off and the resin was washed six times with DMF or DCM and then dried.

The completeness of the modification at the N-terminus of the peptide or of the side chain was checked by means of the Kaiser test. To that end, some resin was incubated at 95° C. with 0.28 mol/l ninhydrin (Riedel de Haen, Seelze, Germany) in ethanol (Carl Roth GmbH+Co. KG, Karlsruhe, Germany), 0.2 mmol/l potassium cyanide in pyridine and 76% phenol in ethanol in the ratio (1:1:2). If a blue colouration occurred, which indicates free primary amino groups, the coupling was repeated.

3. Coupling of the Polyethylene Glycol:

Because polyethylene glycol has hygroscopic properties, it was dried under a high vacuum before each coupling reaction.

The following polyethylene glycol derivatives (all Iris Biotech GmbH, Marktredwitz, Germany, >95% purity) were used as starting materials for the couplings described below:

| | |
|---|---|
| α-Methoxy-ω-carboxylic acid polyethylene glycol (20000 Da) | MeO—PEG$^{20000}$—COOH |
| α-Methoxy-ω-carboxylic acid polyethylene glycol (750 Da) | MeO—PEG$^{750}$—COOH |
| α-Methoxy-ω-carboxylic acid polyethylene glycol (5000 Da) | MeO—PEG$^{5000}$—COOH |
| α-Methoxy-ω-mercapto polyethylene glycol (750 Da) | MeO—PEG$^{750}$—SH |
| α-Methoxy-ω-mercapto polyethylene glycol (5000 Da) | MeO—PEG$^{5000}$—SH | a.) Coupling of Polyethylene Glycol with a Free Acid Group (sPEG, e.g. for MeO-PEG-COOH) via DIC and HOBt:

The resin (1 eq.) was first swollen for 20 minutes in DMF. The polyethylene glycol derivative (5 eq.) dissolved in HOBt/DMF (0.5 mol/l, 5 eq.) was then added, and the reaction was activated with DIC (5 eq.). The reaction mixture was then incubated for one hour at RT and with shaking. DIC (2.5 eq.) was then added again, and incubation was carried out for a further 30 minutes. When the reaction was complete, the reaction solution was separated off and the resin was washed six times with DMF. Complete coupling was checked by means of the Kaiser test.

b.) Coupling after Activation of the Polyethylene Glycol, in Particular for PEG$^{5000}$ and Greater:

Here, the polyethylene glycol derivative with a free acid group was first activated as N-hydroxysuccinimide (NHS) ester and then coupled in solution.

To form the active ester, the polyethylene glycol (1 eq.) was incubated at room temperature, with shaking, with in each case 1 eq. of the DCC and N-hydroxysuccinimide previously dissolved in DMF until, after three hours, a fine precipitate formed. The PEG active ester (1 eq.) dissolved in the supernatant was added to the peptide (0.9 eq.) and incubated at RT, with shaking, in PBS (pH=7.4) or DMF. The reaction was monitored by means of RP-HPLC and MALDI-TOF-MS or by LC-MS.

c.) Thioether Ligation with Thiol-Modified Polyethylene Glycol (tPEG):

A thiol-derivatised polyethylene glycol (e.g. MeO-PEG-SH) (1 eq.) was added to the iodoacetylated peptide (4 eq.) in PBS (pH=7.4), the reaction solution was degassed, and incubation was carried out under an $N_2$ atmosphere at 4° C. for 18 hours. The progress of the reaction was monitored by means of RP-HPLC and MALDI-TOF-MS.

The PEGylated peptides were obtained in a yield of from 25 to 40% and characterized by means of RP-HPLC and MALDI-MS.

TABLE 4

Overview of the synthesised peptide sequences

| SEQ ID No. | Name | Sequence |
|---|---|---|
| 2 | Api 1b* | GNNRPVYIPQPRPPHPRL-OH |
| 14 | Api 88* | Guan-ONNRPVYIPRPRPPHPRL-NH$_2$ |
| 15 | Api 134* | Guan-ONNRPVYIPRPRPPHPOL-NH$_2$ |
| 16 | Api 137* | Guan-ONNRPVYIPRPRPPHPRL-OH |
| 17 | Api 137 (sPEG$^{750}$) | Guan-O(sPEG$^{750}$)NNRPVYIPRPRPPHPRL-OH |
| 18 | Api 137 (SG)* | Guan-O(SG)NNRPVYIPRPRPPHPRL-OH |
| 19 | Api 137 (GRSG)* | Guan-O(GRSG)NNRPVYIPRPRPPHPRL-OH |
| 20 | Api 137 (GARSG)* | Guan-O(GARSG)NNRPVYIPRPRPPHPRL-OH |
| 21 | Api 137 (sPEG$^{750}$-GRSG) | Guan-O(sPEG$^{750}$-GRSG)NNRPVYIPRPRPPHPRL-OH |
| 22 | Api 137 (sPEG$^{750}$-GARSG) | Guan-O(sPEG$^{750}$-GARSG)NNRPVYIPRPRPPHPRL-OH |
| 23 | Api 137 (sPEG$^{5000}$-GARSG) | Guan-O(sPEG$^{5000}$-GARSG)NNRPVYIPRPRPPHPRL-OH |
| 24 | Api 137 (sPEG$^{20000}$-GARSG) | Guan-O(sPEG$^{20000}$-GARSG)NNRPVYIPRPRPPHPRL-OH |
| 25 | Api 300 (SG)$^+$ | Guan-OO(SG)NRPVYIPRPRPPHPRL-OH |
| 26 | Api 300 (GRSG)* | Guan-OO(GRSG)NRPVYIPRPRPPHPRL-OH |
| 27 | Api 300 (GARSG)* | Guan-OO(GARSG)NRPVYIPRPRPPHPRL-OH |
| 28 | Api 300 (GAARSG)* | Guan-OO(GAARSG)NRPVYIPRPRPPHPRL-OH |
| 29 | Api 300 (sPEG$^{750}$-GRSG) | Guan-OO(sPEG$^{750}$-GRSG)NRPVYIPRPRPPHPRL-OH |
| 30 | Api 300 (sPEG$^{750}$-GARSG) | Guan-OO(sPEG$^{750}$-GARSG)NRPVYIPRPRPPHPRL-OH |
| 31 | Api 300 (sPEG$^{750}$-GAARSG) | Guan-OO(sPEG$^{750}$-GAARSG)NRPVYIPRPRPPHPRL-OH |
| 32 | Api 300 (tPEG$^{750}$-GRSG) | Guan-OO(tPEG$^{750}$-GRSG)NRPVYIPRPRPPHPRL-OH |
| 33 | Api 300 (tPEG$^{750}$-GARSG) | Guan-OO(tPEG$^{750}$-GARSG)NRPVYIPRPRPPHPRL-OH |
| 34 | Api 300 (tPEG$^{750}$-GAARSG) | Guan-OO(tPEG$^{750}$-GAARSG)NRPVYIPRPRPPHPRL-OH |
| 35 | Api 300 (tPEG$^{5000}$-GRSG) | Guan-OO(tPEG$^{5000}$-GRSG)NRPVYIPRPRPPHPRL-OH |
| 36 | Api 300 (tPEG$^{5000}$-GARSG) | Guan-OO(tPEG$^{5000}$-GARSG)NRPVYIPRPRPPHPRL-OH |
| 37 | Api 300 (tPEG$^{5000}$-GAARSG) | Guan-OO(tPEG$^{5000}$-GAARSG)NRPVYIPRPRPPHPRL-OH |
| 38 | Api 301 (SG)$^+$ | Guan-ONO(SG)RPVYIPRPRPPHPRL-OH |
| 39 | Api 301 (GRSG)* | Guan-ONO(GRSG)RPVYIPRPRPPHPRL-OH |
| 40 | Api 301 (GARSG)* | Guan-ONO(GARSG)RPVYIPRPRPPHPRL-OH |
| 41 | Api 301 (GAARSG)* | Guan-ONO(GAARSG)RPVYIPRPRPPHPRL-OH |
| 42 | Api 301 (sPEG$^{750}$-GRSG) | Guan-ONO(sPEG$^{750}$-GRSG)RPVYIPRPRPPHPRL-OH |
| 43 | Api 301 (sPEG$^{750}$-GARSG) | Guan-ONO(sPEG$^{750}$-GARSG)RPVYIPRPRPPHPRL-OH |
| 44 | Api 301 (sPEG$^{750}$-GAARSG) | Guan-ONO(sPEG$^{750}$-GAARSG)RPVYIPRPRPPHPRL-OH |
| 45 | Api 301 (tPEG$^{750}$-GRSG) | Guan-ONO(tPEG$^{750}$-GRSG)RPVYIPRPRPPHPRL-OH |

TABLE 4-continued

Overview of the synthesised peptide sequences

| SEQ ID No. | Name | Sequence |
|---|---|---|
| 46 | Api 301 (tPEG$^{750}$-GARSG) | Guan-ONO(tPEG$^{750}$-GARSG)RPVYIPRPRPPHPRL-OH |
| 47 | Api 301 (tPEG$^{750}$-GAARSG) | Guan-ONO(tPEG$^{750}$-GAARSG)RPVYIPRPRPPHPRL-OH |
| 48 | Api 301 (tPEG$^{5000}$-GRSG) | Guan-ONO(tPEG$^{5000}$-GRSG)RPVYIPRPRPPHPRL-OH |
| 49 | Api 301 (tPEG$^{5000}$-GARSG) | Guan-ONO(tPEG$^{5000}$-GARSG)RPVYIPRPRPPHPRL-OH |
| 50 | Api 301 (tPEG$^{5000}$-GAARSG) | Guan-ONO(tPEG$^{5000}$-GAARSG)RPVYIPRPRPPHPRL-OH |
| 51 | Onc 72$^+$ | VDKPPYLPRPRPPROIYNO-NH$_2$ |
| 52 | Onc 110$^+$ | VDKPPYLPRPRPHypRHypTleYNO-NH$_2$ |
| 53 | GAR-Onc 72* | GAR-VDKPPYLPRPRPPROIYNO-NH$_2$ |
| 54 | GAR-Onc 110* | GAR-VDKPPYLPRPRPHypRHypTleYNO-NH$_2$ |
| 55 | sPEG$^{750}$-GAR-Onc 72 | sPEG$^{750}$-GAR-VDKPPYLPRPRPPROIYNO-NH$_2$ |
| 56 | sPEG$^{750}$-GAR-Onc 110 | sPEG$^{750}$-GAR-VDKPPYLPRPRPHypRHypTleYNO-NH$_2$ |
| 57 | tPEG$^{750}$-GAR-Onc 72* | tPEG$^{750}$-GAR-VDKPPYLPRPRPPROIYNO-NH$_2$ |
| 58 | tPEG$^{750}$-GAR-Onc 110 | tPEG$^{750}$-GAR-VDKPPYLPRPRPHypRHypTleYNO-NH$_2$ |
| 59 | tPEG$^{5000}$-GAR-Onc 72 | tPEG$^{5000}$-GAR-VDKPPYLPRPRPPROIYNO-NH$_2$ |
| 60 | tPEG$^{5000}$-GAR-Onc 110 | tPEG$^{5000}$-GAR-VDKPPYLPRPRPHypRHypTleYNO-NH$_2$ |

Guan = guanidino group at the N-terminus,
Hyp = trans-4-hydroxyproline,
L(N$_3$) = Nα-(9-fluorenylmethyloxycarbonyl)-ε-azido-L-lysine,
O = ornithine,
Pra = Nα-(9-fluorenylmethyloxycarbonyl)-L-progargylglycine,
Tle = L-tertiary-leucine (L-tertiary-butylglycine),
sPEG: PEG linked via acid group,
tPEG: PEG linked via thiol group.
comparison examples are marked with *,
cleavage products are marked with $^+$.

c.) Cleavage of Protecting Groups and Purification:

When the synthesis of the peptides and optional modification were complete, the resins were washed carefully with DMF and DCM and dried. The resin-bonded peptides were cleaved for 4 hours at room temperature with a mixture of water, m-cresol, thioanisole and ethanedithiol (5:5:5:2.5) in 87.5% trifluoroacetic acid (TFA), and at the same time the side chains were deprotected. The peptides and peptide derivatives were precipitated with cold diethyl ether and centrifuged off at 3000×g. The pellet was washed twice with cold ether, dried and dissolved in 0.1% aqueous TFA (UV spectroscopy). The samples were stored at −20° C.

The cleaved (optionally modified) peptides were purified by means of RP-HPLC on an Äkta HPLC System (Amersham Bioscience GmbH, Freiburg, Germany) with a Jupiter C$_{18}$ 5 µm 300 Å, 250×10 mm or Jupiter C$_{18}$ 15 µm, 300 Å, 250×21 mm column (Phenomenex Inc., Torrance, USA).

As eluent there was used in each case 0.1% aqueous TFA (eluent A) and 60% aqueous acetonitrile (Biosolve BV, Valkenswaard, Netherlands) with 0.1% TFA (eluent B). A typical linear gradient began at 5% B and the elution took place at a gradient of 1% B per minute with a flow rate of 10 ml/min (250×21 mm column) or 5 ml/min (250×10 mm column). Detection was at 220, 230 and 240 nm. Analysis of the purified peptides was carried out with the same HPLC system with a Jupiter C$_{18}$ 5 µm, 300 Å, 150×4.6 mm column (Phenomenex Inc., Torrance, USA). Elution was carried out at a flow rate of 1 ml/min with a linear gradient of 5-95% B in 30 minutes, and detection was at 220 nm. In addition, the purity was determined by means of matrix-assisted laser desorption/ionisation with time-of-flight mass spectrometry (MALDI-TOF-MS; 4700 Proteomic Analyzer, Applied Biosystems GmbH, Darmstadt, Germany). To that end, 0.5 µl of peptide solution was co-crystallised with 0.5 µl of α-cyanohydroxy-cinnamic acid (Bruker Daltonik GmbH; Bremen, Germany) as matrix (4 mg/ml in 60% acetonitrile in 0.1% aqueous TEA).

Example 2

Determination of the Minimum Inhibitory Concentrations and Growth Kinetics

1. Minimum Inhibitory Concentrations:

The minimum inhibitory concentrations (MIC) of the peptides were determined in a double determination of triplicates with a positive control (gentamycin) and a negative control (0.9% NaCl solution).

To that end, the peptides were dissolved in water and diluted in a two-fold dilution series with 1% aqueous soybean medium (TSB) in sterile 96-well plates (Greiner Bio-One GmbH) from 128 µg/ml in twelve dilution steps to 62.5 ng/ml.

Overnight cultures of *Escherichia coli* strain BL21AI were adjusted with 1% TSB to about $1.5 \times 10^7$ colony forming units per ml. In each case 50 µl of peptide solution per well were then mixed with in each case 50 µl of the bacteria solution, in order to achieve a starting concentration of $4 \times 10^5$ bacteria per well. After incubation for 20 hours at 37° C., the absorption at 595 nm was determined (microplate reader, TECAN Trading AG). The minimum inhibitory concentration was identified as the lowest peptide concentration at which no bacterial growth was demonstrated.

In addition, the antibacterial activity was also determined in the presence of 25% mouse serum. To that end, the MIC values were determined as described above, but 25 µl of mouse serum were also added to each well before the incubation (25% final concentration).

TABLE 5

Minimum inhibitory concentrations

| Seq. ID | Peptide derivative | MIC [µmol/l] in TSB | MIC [µmol/l] in TSB/mouse serum |
|---|---|---|---|
| 2 | Apidaecin 1b* | 0.48 | 1.75 |
| 14 | Api 88* | 0.44 | 1.19 |
| 15 | Api 134* | 1.78 | 7.12 |
| 16 | Api 137* | 0.46 | 0.23 |
| 18 | Api 137 (SG)+ | 0.2 | |
| 19 | Api 137 (GRSG)* | 0.7 | |
| 20 | Api 137 (GARSG)* | 0.9 | |
| 22 | Api 137 (sPEG$^{750}$-GARSG) | 1.1 | |
| 23 | Api 137 (sPEG$^{5000}$-GARSG) | 3.7 | |
| 24 | Api 137 (sPEG$^{20000}$-GARSG) | 10.2 | |
| 25 | Api 300 (SG)+ | 0.8 | 0.21 |
| 29 | Api 300 (sPEG$^{750}$-GRSG) | 2.9 | 0.37 |
| 30 | Api 300 (sPEG$^{750}$-GARSG) | 2.9 | 0.54 |
| 31 | Api 300 (sPEG$^{750}$-GAARSG) | 2.8 | |
| 32 | Api 300 (tPEG$^{750}$-GRSG) | 2.9 | |
| 33 | Api 300 (tPEG$^{750}$-GARSG) | 1.5 | |
| 34 | Api 300 (tPEG$^{750}$-GAARSG) | 2.8 | |
| 35 | Api 300 (tPEG$^{5000}$-GRSG) | >44.8 | |
| 36 | Api 300 (tPEG$^{5000}$-GARSG) | 17.4 | 0.44 |
| 37 | Api 300 (tPEG$^{5000}$-GAARSG) | 25.4 | |
| 38 | Api 301 (SG)+ | 1.6 | |
| 42 | Api 301 (sPEG$^{750}$-GRSG) | 1.5 | |
| 43 | Api 301 (sPEG$^{750}$-GARSG) | 2.9 | 0.27 |
| 44 | Api 301 (sPEG$^{750}$-GAARSG) | 5.6 | |
| 45 | Api 301 (tPEG$^{750}$-GRSG) | 2.9 | |
| 46 | Api 301 (tPEG$^{750}$-GARSG) | 1.5 | |
| 47 | Api 301 (tPEG$^{750}$-GAARSG) | 2.8 | |
| 48 | Api 301 (tPEG$^{5000}$-GRSG) | >38 | |
| 49 | Api 301 (tPEG$^{5000}$-GARSG) | 9.2 | |
| 50 | Api 301 (tPEG$^{5000}$-GAARSG) | >47.5 | |
| 51 | Onc 72+ | 1.7 | 1.7 |
| 53 | GAR-Onc 72* | 3.1 | |
| 55 | sPEG750-GAR-Onc 72 | 12.2 | 6.1 |
| 57 | tPEG750-GAR-Onc 72 | 24.3 | |
| 52 | Onc 110+ | 6.9 | |
| 54 | GAR-Onc 110* | 1.5 | 0.65 |
| 56 | sPEG$^{750}$-GAR-Onc 110 | 24.3 | 9.2 |
| 58 | tPEG$^{750}$-GAR-Onc 110 | 48.4 | | comparison examples are marked with *, cleavage products are marked with +.

Owing to the large difference in mass between the unmodified and the PEG-coupled peptides, the MIC is not given in the conventional unit µg/ml but in µmol/l.

The results show that the presence of the peptide linker (GAR-Onc 72 and GAR-Onc 120) or residues thereof remaining in the cleavage product (Api 137 (SG), Api 300 (SG) and Api 301 (SG)) does not increase the MIC or increases it only insignificantly. In the PEG-modified peptides, the MIC in TSB increases with the size of the PEG. Without serum (TSB), the PEG-modified peptides exhibit an increased MIC. In the serum, the PEG-modified peptides have, however, a MIC which is comparable with the unpegylated peptides.

Example 3

Release of the Peptide Active Ingredients in Serum

1. Analysis in Mouse Serum:

30 µl of a 1 mg/ml peptide solution were diluted with 120 µl of water and, after addition of 50 µl of serum, incubated at 37° C. for 0 hours, 0.5 hour, 1 hour, 2 hours or 4 hours. Alternatively, the peptide derivatives having a starting concentration of 3 mg/ml were diluted with serum to a final concentration of 15 µg/ml. According to the stability of the peptides, the samples were analysed at the times mentioned above or after 0 hours, 4 hours and 6 hours. The serum proteins were precipitated by addition of 50 µl of 15% TCA, and the supernatant was neutralised with 25 µl of 1 mol/l NaOH. The samples were made up to 250 µl with 5% B, 230 µl of the solution were transferred into a HPLC vial, and 220 µl were injected.

RP-HPLC analysis was carried out with a linear acetonitrile gradient (Biosolve BV, Valkenswaard, Netherlands) in the presence of 0.1% trifluoroacetic acid (TFA, UV grade, Fluka Chemie GmbH, Buchs, Switzerland) as ion-pair reagent. The fractions were co-crystallised with α-cyanohydroxycinnamic acid (Bruker Daltonik GmbH; Bremen, Germany) as matrix (4 mg/ml in 60% acetonitrile in 0.1% aqueous TFA) and analysed with a tandem mass spectrometer (MALDI-TOF/TOF-MS, 4700 Proteomics Analyzer; Applied Biosystems GmbH, Weiterstadt, Germany) in positive-ion reflector mode. The amount of intact peptides and their degradation products or metabolites could thus be identified and quantified at the individual times. 25% aqueous mouse serum, which was analysed in parallel for the same time intervals, was used as control.

TABLE 6

Overview of the half-lives in 25% (v/v) and pure mouse serum, the different side-chain modifications in combination with PEG750 were compared; primary (red) and secondary cleavage site (blue), the half-lives marked with * were quantified by means of MALDI-TOF MS.

| Seq. ID | Peptide derivative | Half-life ($t_{1/2}$) in 25% serum | in serum |
|---|---|---|---|
| 16 | Api 137* | >360 min | |
| 18 | Api 137 (GRSG)* | 60 min | |
| 20 | Api 137 (GARSG)* | 30 min | |
| 21 | Api 137 (sPEG$^{750}$-GRSG) | 120 min | |
| 22 | Api 137 (sPEG$^{750}$-GARSG) | 60 min | |
| 25 | Api 300 (SG)+ | | 240 min |
| 29 | Api 300 (sPEG$^{750}$-GRSG) | | 50 min |
| 32 | Api 300 (tPEG$^{750}$-GRSG) | | 40 min |
| 35 | Api 300 (tPEG$^{5000}$-GRSG) | | 75% (6 h)** |
| 30 | Api 300 (sPEG$^{750}$-GARSG) | | 35 min |
| 33 | Api 300 (tPEG$^{750}$-GARSG) | | 45 min |
| 36 | Api 300 (tPEG$^{5000}$-GARSG) | | 69% (6 h)** |
| 31 | Api 300 (sPEG$^{750}$-GAARSG) | | 45 min |
| 34 | Api 300 (tPEG$^{750}$-GAARSG) | | 35 min |
| 37 | Api 300 (tPEG$^{5000}$-GAARSG) | | 76% (6 h)** |
| 38 | Api 301 (SG)+ | | 60% (4 h)** |
| 42 | Api 301 (sPEG$^{750}$-GRSG) | | 30 min |
| 45 | Api 301 (tPEG$^{750}$-GRSG) | | 55 min |
| 48 | Api 301 (tPEG$^{5000}$-GRSG) | | 75% (6 h)** |
| 43 | Api 301 (sPEG$^{750}$-GARSG) | | 45 min |
| 46 | Api 301 (tPEG$^{750}$-GARSG) | | 45 min |
| 49 | Api 301 (tPEG$^{5000}$-GARSG) | | 62% (6 h)** |
| 44 | Api 301 (sPEG$^{750}$-GAARSG) | | 55 min |

TABLE 6-continued

Overview of the half-lives in 25% (v/v) and pure mouse serum, the different side-chain modifications in combination with PEG750 were compared; primary (red) and secondary cleavage site (blue), the half-lives marked with * were quantified by means of MALDI-TOF MS.

| Seq. ID | Peptide derivative | Half-life ($t_{1/2}$) in 25% serum | in serum |
|---|---|---|---|
| 47 | Api 301 (tPEG$^{750}$-GAARSG) | | 50 min |
| 50 | Api 301 (tPEG$^{5000}$-GAARSG) | | 78% (5 h)** |
| 51 | GAR-Onc 72* | | 85% (4 h)** |
| 52 | GAR-Onc 110* | | 75% (4 h)** |
| 55 | sPEG$^{750}$-GAR-Onc 72 | | 6 h |
| 56 | sPEG$^{750}$-GAR-Onc 110 | | 73% (6 h)** |
| 57 | tPEG$^{750}$-GAR-Onc 72 | | 55% (6 h)** |
| 58 | tPEG$^{750}$-GAR-Onc 110 | | 64% (6 h)** |
| 59 | tPEG$^{5000}$-GAR-Onc 72 | | 86% (6 h)** |
| 60 | tPEG$^{5000}$-GAR-Onc 110 | | 96% (6 h)** | comparison examples are marked with *, cleavage products are marked with †.
**uncleaved peptide remaining after the indicated time (instead of half-life)

The half-lives (or uncleaved peptide remaining after the indicated time) relate in the case of the free peptides (Api 137, Api300 (SG) and Api 301 (SG)) to the cleavage site in the peptide (downstream of Arg-16). In the case of the remaining derivatives, the values relate to the cleavage in the linker in the side chain with release of Api 137 (SG), Api300 (SG) and Api 301 (SG) or of Onc 72 and Onc 110.

The following abbreviations are used in the description of the invention:

Agp 2-amino-3-guanidinopropionic acid
BOC tert-butyloxy-carbonyl
$^t$Bu tert-butyl ether
Dap 2,3-diaminopropionic acid
DCC dicyclohexylcarbodiimide
DCM dichloromethane
DIC diisopropylcarbodiimide
DMF dimethylformamide
*E. coli* *Escherichia coil*
eq. equivalents per mol.
Fmoc fluorenylmethoxycarbonyl
Guan guanidino group (at the N-terminus)
Hyp trans-4-hydroxyproline
HBTU 2-(1H-benzotriazol-1-yl)-1,1,3,3-tetramethyluronium hexafluorophosphate
HOBt 1-hydroxybenzotriazole
LC-MS liquid chromatography with mass spectrometry coupling
MALDI-TOF matrix assisted laser desorption/ionization with time of flight analysis
MIC minimum inhibitory concentration
MS mass spectrometry
Mtt 4-methyltrityl
NHS N-hydroxysuccinimide
NMM N-methylmorpholine
O ornithine
O$^t$Bu tert-butyl ester
PBS phosphate-buffered saline
PEG polyethylene glycol
sPEG PEG linked via an acid group
tPEG PEG linked via a thiol group
Pra Nα-(9-fluorenylmethyloxycarbonyl)-L-progargylglycine
RP-HPLC reversed phase high performance liquid chromatography
RT room temperature
TCA trichloroacetic acid
TFA trifluoroacetic acid
Tle L-tertiary-leucine (L-tertiary-butylglycine)
Tris tris(hydroxymethyl)-aminomethane
TSB tryptic soy broth

```
                        SEQUENCE LISTING

<160> NUMBER OF SEQ ID NOS: 83

<210> SEQ ID NO 1
<211> LENGTH: 18
<212> TYPE: PRT
<213> ORGANISM: Apis mellifera

<400> SEQUENCE: 1

Gly Asn Asn Arg Pro Val Tyr Ile Pro Gln Pro Arg Pro Pro His Pro
1               5                   10                  15

Arg Ile

<210> SEQ ID NO 2
<211> LENGTH: 18
<212> TYPE: PRT
<213> ORGANISM: Apis mellifera

<400> SEQUENCE: 2

Gly Asn Asn Arg Pro Val Tyr Ile Pro Gln Pro Arg Pro Pro His Pro
1               5                   10                  15

Arg Leu

<210> SEQ ID NO 3
<211> LENGTH: 19
<212> TYPE: PRT
<213> ORGANISM: Drosophila melanogaster
```

-continued

<400> SEQUENCE: 3

Gly Lys Pro Arg Pro Tyr Ser Pro Arg Pro Thr Ser His Pro Arg Pro
1               5                   10                  15

Ile Arg Val

<210> SEQ ID NO 4
<211> LENGTH: 16
<212> TYPE: PRT
<213> ORGANISM: Myrmecia gulosa

<400> SEQUENCE: 4

Gly Arg Pro Asn Pro Val Asn Asn Lys Pro Thr Pro Tyr Pro His Leu
1               5                   10                  15

<210> SEQ ID NO 5
<211> LENGTH: 20
<212> TYPE: PRT
<213> ORGANISM: Pyrrhocoris apterus
<220> FEATURE:
<221> NAME/KEY: misc_feature
<222> LOCATION: (20)..(20)
<223> OTHER INFORMATION: Xaa is asparagine amide

<400> SEQUENCE: 5

Val Asp Lys Gly Ser Tyr Leu Pro Arg Pro Thr Pro Pro Arg Pro Ile
1               5                   10                  15

Tyr Asn Arg Xaa
            20

<210> SEQ ID NO 6
<211> LENGTH: 15
<212> TYPE: PRT
<213> ORGANISM: Palomena prasina

<400> SEQUENCE: 6

Val Asp Lys Pro Asp Tyr Arg Pro Arg Pro Arg Pro Pro Asn Met
1               5                   10                  15

<210> SEQ ID NO 7
<211> LENGTH: 34
<212> TYPE: PRT
<213> ORGANISM: Oncopeltus fasciatus

<400> SEQUENCE: 7

Glu Val Ser Leu Lys Gly Glu Gly Gly Ser Asn Lys Gly Phe Ile Gln
1               5                   10                  15

Gly Ser Gly Thr Lys Thr Leu Phe Gln Asp Asp Lys Thr Lys Leu Asp
            20                  25                  30

Gly Thr

<210> SEQ ID NO 8
<211> LENGTH: 20
<212> TYPE: PRT
<213> ORGANISM: Oncopeltus fasciatus
<220> FEATURE:
<221> NAME/KEY: misc_feature
<222> LOCATION: (11)..(11)
<223> OTHER INFORMATION: Xaa is Pro or any other naturally occurring
      amino acid
<220> FEATURE:
<221> NAME/KEY: misc_feature
<222> LOCATION: (19)..(20)
<223> OTHER INFORMATION: Optional residues

<400> SEQUENCE: 8

```
Val Asp Lys Pro Pro Tyr Leu Pro Arg Pro Xaa Pro Pro Arg Arg Ile
1               5                   10                  15

Tyr Asn Asn Arg
            20

<210> SEQ ID NO 9
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is ornithine
<220> FEATURE:
<221> NAME/KEY: misc_feature
<222> LOCATION: (3)..(3)
<223> OTHER INFORMATION: Xaa is ornithine

<400> SEQUENCE: 9

Xaa Asn Xaa Arg Pro Val Tyr Ile Pro Arg Pro Arg Pro Pro His Pro
1               5                   10                  15

Arg Leu

<210> SEQ ID NO 10
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is ornithine
<220> FEATURE:
<221> NAME/KEY: misc_feature
<222> LOCATION: (2)..(2)
<223> OTHER INFORMATION: Xaa is ornithine

<400> SEQUENCE: 10

Xaa Xaa Asn Arg Pro Val Tyr Ile Pro Arg Pro Arg Pro Pro His Pro
1               5                   10                  15

Arg Leu

<210> SEQ ID NO 11
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is ornithine

<400> SEQUENCE: 11

Xaa Asn Asn Arg Pro Val Tyr Ile Pro Arg Pro Arg Pro Pro His Pro
1               5                   10                  15

Arg Leu

<210> SEQ ID NO 12
<211> LENGTH: 19
<212> TYPE: PRT
<213> ORGANISM: Artificial Sequence
<220> FEATURE:
<223> OTHER INFORMATION: Synthesized Peptide
```

```
<220> FEATURE:
<221> NAME/KEY: misc_feature
<222> LOCATION: (15)..(15)
<223> OTHER INFORMATION: Xaa is ornithine
<220> FEATURE:
<221> NAME/KEY: misc_feature
<222> LOCATION: (19)..(19)
<223> OTHER INFORMATION: Xaa is ornithine amide

<400> SEQUENCE: 12

Val Asp Lys Pro Pro Tyr Leu Pro Arg Pro Arg Pro Pro Arg Xaa Ile
1               5                   10                  15

Tyr Asn Xaa

<210> SEQ ID NO 13
<211> LENGTH: 19
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (13)..(13)
<223> OTHER INFORMATION: Xaa is 4-hydroxyproline
<220> FEATURE:
<221> NAME/KEY: misc_feature
<222> LOCATION: (15)..(15)
<223> OTHER INFORMATION: Xaa is 4-hydroxyproline
<220> FEATURE:
<221> NAME/KEY: misc_feature
<222> LOCATION: (16)..(16)
<223> OTHER INFORMATION: Xaa is tert-leucine
<220> FEATURE:
<221> NAME/KEY: misc_feature
<222> LOCATION: (19)..(19)
<223> OTHER INFORMATION: Xaa is ornithine amide

<400> SEQUENCE: 13

Val Asp Lys Pro Pro Tyr Leu Pro Arg Pro Arg Pro Xaa Arg Xaa Xaa
1               5                   10                  15

Tyr Asn Xaa

<210> SEQ ID NO 14
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (18)..(18)
<223> OTHER INFORMATION: Xaa is leucine amide

<400> SEQUENCE: 14

Xaa Asn Asn Arg Pro Val Tyr Ile Pro Arg Pro Arg Pro Pro His Pro
1               5                   10                  15

Arg Xaa

<210> SEQ ID NO 15
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
```

```
<222> LOCATION: (1)..(1)
<223> OTHER INFORMATION: Xaa is N-guanido-ornithine
<220> FEATURE:
<221> NAME/KEY: misc_feature
<222> LOCATION: (17)..(17)
<223> OTHER INFORMATION: Xaa is ornithine
<220> FEATURE:
<221> NAME/KEY: misc_feature
<222> LOCATION: (18)..(18)
<223> OTHER INFORMATION: Xaa is leucine amide

<400> SEQUENCE: 15

Xaa Asn Asn Arg Pro Val Tyr Ile Pro Arg Pro Arg Pro Pro His Pro
1               5                   10                  15

Xaa Xaa

<210> SEQ ID NO 16
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine

<400> SEQUENCE: 16

Xaa Asn Asn Arg Pro Val Tyr Ile Pro Arg Pro Arg Pro Pro His Pro
1               5                   10                  15

Arg Leu

<210> SEQ ID NO 17
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-Orn with PEG750 linked to Orn
      delta-NH2

<400> SEQUENCE: 17

Xaa Asn Asn Arg Pro Val Tyr Ile Pro Arg Pro Arg Pro Pro His Pro
1               5                   10                  15

Arg Leu

<210> SEQ ID NO 18
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-Orn with SG linker bound to
      Orn delta-NH2

<400> SEQUENCE: 18

Xaa Asn Asn Arg Pro Val Tyr Ile Pro Arg Pro Arg Pro Pro His Pro
1               5                   10                  15

Arg Leu

<210> SEQ ID NO 19
```

```
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-Orn with GRSG linker bound to
      Orn delta-NH2

<400> SEQUENCE: 19

Xaa Asn Asn Arg Pro Val Tyr Ile Pro Arg Pro Arg Pro Pro His Pro
1               5                   10                  15

Arg Leu

<210> SEQ ID NO 20
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-Orn with GARSG linker bound to
      Orn delta-NH2

<400> SEQUENCE: 20

Xaa Asn Asn Arg Pro Val Tyr Ile Pro Arg Pro Arg Pro Pro His Pro
1               5                   10                  15

Arg Leu

<210> SEQ ID NO 21
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-Orn with N-PEG750-GARSG bound
      to Orn delta-NH2

<400> SEQUENCE: 21

Xaa Asn Asn Arg Pro Val Tyr Ile Pro Arg Pro Arg Pro Pro His Pro
1               5                   10                  15

Arg Leu

<210> SEQ ID NO 22
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-Orn with N-PEG750-GARSG bound
      to Orn delta-NH2

<400> SEQUENCE: 22

Xaa Asn Asn Arg Pro Val Tyr Ile Pro Arg Pro Arg Pro Pro His Pro
1               5                   10                  15

Arg Leu
```

```
<210> SEQ ID NO 23
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-Orn with N-PEG5000-GARSG bound
      to Orn delta-NH2

<400> SEQUENCE: 23

Xaa Asn Asn Arg Pro Val Tyr Ile Pro Arg Pro Arg Pro Pro His Pro
1               5                   10                  15

Arg Leu

<210> SEQ ID NO 24
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-Orn with N-PEG20000-GARSG
      bound to Orn delta-NH2

<400> SEQUENCE: 24

Xaa Asn Asn Arg Pro Val Tyr Ile Pro Arg Pro Arg Pro Pro His Pro
1               5                   10                  15

Arg Leu

<210> SEQ ID NO 25
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (2)..(2)
<223> OTHER INFORMATION: Xaa is Orn with SG linker bound to Orn
      delta-NH2

<400> SEQUENCE: 25

Xaa Xaa Asn Arg Pro Val Tyr Ile Pro Arg Pro Arg Pro Pro His Pro
1               5                   10                  15

Arg Leu

<210> SEQ ID NO 26
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (2)..(2)
<223> OTHER INFORMATION: Xaa is Orn with GASG linker bound to Orn
      delta-NH2
```

-continued

<400> SEQUENCE: 26

Xaa Xaa Asn Arg Pro Val Tyr Ile Pro Arg Pro Arg Pro Pro His Pro
1               5                   10                  15

Arg Leu

<210> SEQ ID NO 27
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (2)..(2)
<223> OTHER INFORMATION: Xaa is Orn with GARSG linker bound to Orn
      delta-NH2

<400> SEQUENCE: 27

Xaa Xaa Asn Arg Pro Val Tyr Ile Pro Arg Pro Arg Pro Pro His Pro
1               5                   10                  15

Arg Leu

<210> SEQ ID NO 28
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (2)..(2)
<223> OTHER INFORMATION: Xaa is Orn with GAARSG linker bound to Orn
      delta-NH2

<400> SEQUENCE: 28

Xaa Xaa Asn Arg Pro Val Tyr Ile Pro Arg Pro Arg Pro Pro His Pro
1               5                   10                  15

Arg Leu

<210> SEQ ID NO 29
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (2)..(2)
<223> OTHER INFORMATION: Xaa is Orn with N-PEG750-GRSG bound to Orn
      delta-NH2

<400> SEQUENCE: 29

Xaa Xaa Asn Arg Pro Val Tyr Ile Pro Arg Pro Arg Pro Pro His Pro
1               5                   10                  15

Arg Leu

<210> SEQ ID NO 30
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (2)..(2)
<223> OTHER INFORMATION: Xaa is Orn with N-PEG750-GARSG bound to Orn
      delta-NH2

<400> SEQUENCE: 30

Xaa Xaa Asn Arg Pro Val Tyr Ile Pro Arg Pro Arg Pro Pro His Pro
1               5                   10                  15

Arg Leu

<210> SEQ ID NO 31
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (2)..(2)
<223> OTHER INFORMATION: Xaa is Orn with N-PEG750-GAARSG bound to Orn
      delta-NH2

<400> SEQUENCE: 31

Xaa Xaa Asn Arg Pro Val Tyr Ile Pro Arg Pro Arg Pro Pro His Pro
1               5                   10                  15

Arg Leu

<210> SEQ ID NO 32
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (2)..(2)
<223> OTHER INFORMATION: Xaa is Orn with tPEG750-GRSG bound to Orn
      delta-NH2

<400> SEQUENCE: 32

Xaa Xaa Asn Arg Pro Val Tyr Ile Pro Arg Pro Arg Pro Pro His Pro
1               5                   10                  15

Arg Leu

<210> SEQ ID NO 33
<211> LENGTH: 18
<212> TYPE: PRT
<213> ORGANISM: Artificial Sequence
<220> FEATURE:

```
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (2)..(2)
<223> OTHER INFORMATION: Xaa is Orn with tPEG750-GARSG bound to Orn
      delta-NH2

<400> SEQUENCE: 33

Xaa Xaa Asn Arg Pro Val Tyr Ile Pro Arg Pro Arg Pro Pro His Pro
1               5                   10                  15

Arg Leu

<210> SEQ ID NO 34
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (2)..(2)
<223> OTHER INFORMATION: Xaa is Orn with tPEG750-GAARSG bound to Orn
      delta-NH2

<400> SEQUENCE: 34

Xaa Xaa Asn Arg Pro Val Tyr Ile Pro Arg Pro Arg Pro Pro His Pro
1               5                   10                  15

Arg Leu

<210> SEQ ID NO 35
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (2)..(2)
<223> OTHER INFORMATION: Xaa is Orn with tPEG5000-GRSG bound to Orn
      delta-NH2

<400> SEQUENCE: 35

Xaa Xaa Asn Arg Pro Val Tyr Ile Pro Arg Pro Arg Pro Pro His Pro
1               5                   10                  15

Arg Leu

<210> SEQ ID NO 36
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
```

-continued

```
<222> LOCATION: (2)..(2)
<223> OTHER INFORMATION: Xaa is Orn with tPEG5000-GARSG bound to Orn
      delta-NH2

<400> SEQUENCE: 36

Xaa Xaa Asn Arg Pro Val Tyr Ile Pro Arg Pro Arg Pro Pro His Pro
1               5                   10                  15

Arg Leu

<210> SEQ ID NO 37
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (2)..(2)
<223> OTHER INFORMATION: Xaa is Orn with tPEG5000-GAARSG bound to Orn
      delta-NH2

<400> SEQUENCE: 37

Xaa Xaa Asn Arg Pro Val Tyr Ile Pro Arg Pro Arg Pro Pro His Pro
1               5                   10                  15

Arg Leu

<210> SEQ ID NO 38
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (3)..(3)
<223> OTHER INFORMATION: Xaa is Orn with Ser-Gly bound to Orn delta-NH2

<400> SEQUENCE: 38

Xaa Asn Xaa Arg Pro Val Tyr Ile Pro Arg Pro Arg Pro Pro His Pro
1               5                   10                  15

Arg Leu

<210> SEQ ID NO 39
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (3)..(3)
<223> OTHER INFORMATION: Xaa is Orn with GRSG bound to Orn delta-NH2

<400> SEQUENCE: 39

Xaa Asn Xaa Arg Pro Val Tyr Ile Pro Arg Pro Arg Pro Pro His Pro
1               5                   10                  15
```

Arg Leu

<210> SEQ ID NO 40
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (3)..(3)
<223> OTHER INFORMATION: Xaa is ornithine with GARSG bound to Orn
      delta-NH2

<400> SEQUENCE: 40

Xaa Asn Xaa Arg Pro Val Tyr Ile Pro Arg Pro Arg Pro Pro His Pro
1               5                   10                  15

Arg Leu

<210> SEQ ID NO 41
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (3)..(3)
<223> OTHER INFORMATION: Xaa is Orn with GAARSG bound to Orn delta-NH2

<400> SEQUENCE: 41

Xaa Asn Xaa Arg Pro Val Tyr Ile Pro Arg Pro Arg Pro Pro His Pro
1               5                   10                  15

Arg Leu

<210> SEQ ID NO 42
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (3)..(3)
<223> OTHER INFORMATION: Xaa is Orn with with sPEG750-GRSG bound to Orn
      delta-NH2

<400> SEQUENCE: 42

Xaa Asn Xaa Arg Pro Val Tyr Ile Pro Arg Pro Arg Pro Pro His Pro
1               5                   10                  15

Arg Leu

<210> SEQ ID NO 43
<211> LENGTH: 18
<212> TYPE: PRT
<213> ORGANISM: Artificial Sequence
<220> FEATURE:

<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (3)..(3)
<223> OTHER INFORMATION: Xaa is Orn with sPEG750-GARSG bound to Orn
      delta-NH2

<400> SEQUENCE: 43

Xaa Asn Xaa Arg Pro Val Tyr Ile Pro Arg Pro Arg Pro Pro His Pro
1               5                   10                  15

Arg Leu

<210> SEQ ID NO 44
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (3)..(3)
<223> OTHER INFORMATION: Xaa is Orn with with sPEG750-GAARSG bound to
      Orn delta-NH2

<400> SEQUENCE: 44

Xaa Asn Xaa Arg Pro Val Tyr Ile Pro Arg Pro Arg Pro Pro His Pro
1               5                   10                  15

Arg Leu

<210> SEQ ID NO 45
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-Orn
<220> FEATURE:
<221> NAME/KEY: misc_feature
<222> LOCATION: (3)..(3)
<223> OTHER INFORMATION: Xaa is Orn with tPEG750-GRSG bound to Orn
      delta-NH2

<400> SEQUENCE: 45

Xaa Asn Xaa Arg Pro Val Tyr Ile Pro Arg Pro Arg Pro Pro His Pro
1               5                   10                  15

Arg Leu

<210> SEQ ID NO 46
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature

```
<222> LOCATION: (3)..(3)
<223> OTHER INFORMATION: Xaa is Orn with with tPEG750-GARSG bound to
      Orn delta-NH2

<400> SEQUENCE: 46

Xaa Asn Xaa Arg Pro Val Tyr Ile Pro Arg Pro Arg Pro Pro His Pro
1               5                   10                  15

Arg Leu

<210> SEQ ID NO 47
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (3)..(3)
<223> OTHER INFORMATION: Xaa is Orn with with tPEG750-GAARSG bound to
      Orn delta-NH2

<400> SEQUENCE: 47

Xaa Asn Xaa Arg Pro Val Tyr Ile Pro Arg Pro Arg Pro Pro His Pro
1               5                   10                  15

Arg Leu

<210> SEQ ID NO 48
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (3)..(3)
<223> OTHER INFORMATION: Xaa is Orn with with tPEG5000-GRSG bound to
      Orn delta-NH2

<400> SEQUENCE: 48

Xaa Asn Xaa Arg Pro Val Tyr Ile Pro Arg Pro Arg Pro Pro His Pro
1               5                   10                  15

Arg Leu

<210> SEQ ID NO 49
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (3)..(3)
<223> OTHER INFORMATION: Xaa is Orn with with tPEG5000-GARSG bound to
      Orn delta-NH2

<400> SEQUENCE: 49

Xaa Asn Xaa Arg Pro Val Tyr Ile Pro Arg Pro Arg Pro Pro His Pro
```

```
1               5                   10                  15

Arg Leu

<210> SEQ ID NO 50
<211> LENGTH: 18
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is N-guanido-ornithine
<220> FEATURE:
<221> NAME/KEY: misc_feature
<222> LOCATION: (3)..(3)
<223> OTHER INFORMATION: Xaa is Orn with with tPEG5000-GAARSG bound to
      Orn delta-NH2

<400> SEQUENCE: 50

Xaa Asn Xaa Arg Pro Val Tyr Ile Pro Arg Pro Arg Pro Pro His Pro
1               5                   10                  15

Arg Leu

<210> SEQ ID NO 51
<211> LENGTH: 19
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (15)..(15)
<223> OTHER INFORMATION: Xaa is ornithine
<220> FEATURE:
<221> NAME/KEY: misc_feature
<222> LOCATION: (19)..(19)
<223> OTHER INFORMATION: Xaa is ornithine amide

<400> SEQUENCE: 51

Val Asp Lys Pro Pro Tyr Leu Pro Arg Pro Arg Pro Arg Xaa Ile
1               5                   10                  15

Tyr Asn Xaa

<210> SEQ ID NO 52
<211> LENGTH: 19
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (13)..(13)
<223> OTHER INFORMATION: Xaa is 4-hydroxyproline
<220> FEATURE:
<221> NAME/KEY: misc_feature
<222> LOCATION: (15)..(15)
<223> OTHER INFORMATION: Xaa is 4-hydroxyproline
<220> FEATURE:
<221> NAME/KEY: misc_feature
<222> LOCATION: (16)..(16)
<223> OTHER INFORMATION: Xaa is tert-leucine
<220> FEATURE:
<221> NAME/KEY: misc_feature
<222> LOCATION: (19)..(19)
<223> OTHER INFORMATION: Xaa is ornithine amide

<400> SEQUENCE: 52

Val Asp Lys Pro Pro Tyr Leu Pro Arg Pro Arg Pro Xaa Arg Xaa Xaa
1               5                   10                  15
```

Tyr Asn Xaa

<210> SEQ ID NO 53
<211> LENGTH: 22
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (18)..(18)
<223> OTHER INFORMATION: Xaa is ornithine
<220> FEATURE:
<221> NAME/KEY: misc_feature
<222> LOCATION: (22)..(22)
<223> OTHER INFORMATION: Xaa is ornithine amide

<400> SEQUENCE: 53

Gly Ala Arg Val Asp Lys Pro Pro Tyr Leu Pro Arg Pro Arg Pro Pro
1               5                   10                  15

Arg Xaa Ile Tyr Asn Xaa
            20

<210> SEQ ID NO 54
<211> LENGTH: 22
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (16)..(16)
<223> OTHER INFORMATION: Xaa is 4-hydroxyproline
<220> FEATURE:
<221> NAME/KEY: misc_feature
<222> LOCATION: (18)..(18)
<223> OTHER INFORMATION: Xaa is 4-hydroxyproline
<220> FEATURE:
<221> NAME/KEY: misc_feature
<222> LOCATION: (19)..(19)
<223> OTHER INFORMATION: Xaa is tert-leucine
<220> FEATURE:
<221> NAME/KEY: misc_feature
<222> LOCATION: (22)..(22)
<223> OTHER INFORMATION: Xaa is ornithine amide

<400> SEQUENCE: 54

Gly Ala Arg Val Asp Lys Pro Pro Tyr Leu Pro Arg Pro Arg Pro Xaa
1               5                   10                  15

Arg Xaa Xaa Tyr Asn Xaa
            20

<210> SEQ ID NO 55
<211> LENGTH: 22
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is Gly with PEG750 bound to N-terminus
<220> FEATURE:
<221> NAME/KEY: misc_feature
<222> LOCATION: (18)..(18)
<223> OTHER INFORMATION: Xaa is ornithine
<220> FEATURE:
<221> NAME/KEY: misc_feature
<222> LOCATION: (22)..(22)
<223> OTHER INFORMATION: Xaa is ornithine amide

```
<400> SEQUENCE: 55

Xaa Ala Arg Val Asp Lys Pro Pro Tyr Leu Pro Arg Pro Arg Pro Pro
1               5                   10                  15

Arg Xaa Ile Tyr Asn Xaa
            20

<210> SEQ ID NO 56
<211> LENGTH: 22
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is Gly with PEG750 bound to N-terminus
<220> FEATURE:
<221> NAME/KEY: misc_feature
<222> LOCATION: (16)..(16)
<223> OTHER INFORMATION: Xaa is 4-hydroxyproline
<220> FEATURE:
<221> NAME/KEY: misc_feature
<222> LOCATION: (18)..(18)
<223> OTHER INFORMATION: Xaa is 4-hydroxyproline
<220> FEATURE:
<221> NAME/KEY: misc_feature
<222> LOCATION: (19)..(19)
<223> OTHER INFORMATION: Xaa is tert-leucine
<220> FEATURE:
<221> NAME/KEY: misc_feature
<222> LOCATION: (22)..(22)
<223> OTHER INFORMATION: Xaa is ornithine amide

<400> SEQUENCE: 56

Xaa Ala Arg Val Asp Lys Pro Pro Tyr Leu Pro Arg Pro Arg Pro Xaa
1               5                   10                  15

Arg Xaa Xaa Tyr Asn Xaa
            20

<210> SEQ ID NO 57
<211> LENGTH: 22
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is glycine with thiol-PEG750 bound to
      iodoacetylated N-terminus
<220> FEATURE:
<221> NAME/KEY: misc_feature
<222> LOCATION: (18)..(18)
<223> OTHER INFORMATION: Xaa is ornithine
<220> FEATURE:
<221> NAME/KEY: misc_feature
<222> LOCATION: (22)..(22)
<223> OTHER INFORMATION: Xaa is ornithine amide

<400> SEQUENCE: 57

Xaa Ala Arg Val Asp Lys Pro Pro Tyr Leu Pro Arg Pro Arg Pro Pro
1               5                   10                  15

Arg Xaa Ile Tyr Asn Xaa
            20

<210> SEQ ID NO 58
<211> LENGTH: 22
<212> TYPE: PRT
<213> ORGANISM: Artificial Sequence
<220> FEATURE:
```

```
<223> OTHER INFORMATION: Synthesized Peptide
<220> FEATURE:
<221> NAME/KEY: misc_feature
<222> LOCATION: (1)..(1)
<223> OTHER INFORMATION: Xaa is Gly with thiol-PEG750 bound to
      iodoacetylated N-terminus
<220> FEATURE:
<221> NAME/KEY: misc_feature
<222> LOCATION: (16)..(16)
<223> OTHER INFORMATION: Xaa is 4-hydroxyproline
<220> FEATURE:
<221> NAME/KEY: misc_feature
<222> LOCATION: (18)..(18)
<223> OTHER INFORMATION: Xaa is 4-hydroxyproline
<220> FEATURE:
<221> NAME/KEY: misc_feature
<222> LOCATION: (19)..(19)
<223> OTHER INFORMATION: Xaa is tert-leucine
<220> FEATURE:
<221> NAME/KEY: misc_feature
<222> LOCATION: (22)..(22)
<223> OTHER INFORMATION: Xaa is ornithine amide

<400> SEQUENCE: 58

Xaa Ala Arg Val Asp Lys Pro Pro Tyr Leu Pro Arg Pro Arg Pro Xaa
1               5                   10                  15

Arg Xaa Xaa Tyr Asn Xaa
            20

<210> SEQ ID NO 59
<211> LENGTH: 22
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is Gly with thiol-PEG5000 bound to
      iodoacetylated N-terminus
<220> FEATURE:
<221> NAME/KEY: misc_feature
<222> LOCATION: (18)..(18)
<223> OTHER INFORMATION: Xaa is ornithine
<220> FEATURE:
<221> NAME/KEY: misc_feature
<222> LOCATION: (22)..(22)
<223> OTHER INFORMATION: Xaa is ornithine amide

<400> SEQUENCE: 59

Xaa Ala Arg Val Asp Lys Pro Pro Tyr Leu Pro Arg Pro Arg Pro Pro
1               5                   10                  15

Arg Xaa Ile Tyr Asn Xaa
            20

<210> SEQ ID NO 60
<211> LENGTH: 22
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is Gly with thiol-PEG5000 bound to
      iodoacetylated N-terminus
<220> FEATURE:
<221> NAME/KEY: misc_feature
<222> LOCATION: (16)..(16)
<223> OTHER INFORMATION: Xaa is 4-hydroxyproline
<220> FEATURE:
<221> NAME/KEY: misc_feature
<222> LOCATION: (18)..(18)
```

```
<223> OTHER INFORMATION: Xaa is 4-hydroxyproline
<220> FEATURE:
<221> NAME/KEY: misc_feature
<222> LOCATION: (19)..(19)
<223> OTHER INFORMATION: Xaa is tert-leucine
<220> FEATURE:
<221> NAME/KEY: misc_feature
<222> LOCATION: (22)..(22)
<223> OTHER INFORMATION: Xaa is ornithine amide

<400> SEQUENCE: 60

Xaa Ala Arg Val Asp Lys Pro Pro Tyr Leu Pro Arg Pro Arg Pro Xaa
1               5                   10                  15

Arg Xaa Xaa Tyr Asn Xaa
            20

<210> SEQ ID NO 61
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 61

Gly Arg Ser Gly
1

<210> SEQ ID NO 62
<211> LENGTH: 5
<212> TYPE: PRT
<213> ORGANISM: Artificial Sequence
<220> FEATURE:
<223> OTHER INFORMATION: Synthesized Peptide

<400> SEQUENCE: 62

Gly Ala Arg Ser Gly
1               5

<210> SEQ ID NO 63
<211> LENGTH: 6
<212> TYPE: PRT
<213> ORGANISM: Artificial Sequence
<220> FEATURE:
<223> OTHER INFORMATION: Synthesized Peptide

<400> SEQUENCE: 63

Gly Ala Ala Arg Ser Gly
1               5

<210> SEQ ID NO 64
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 64

Gly Ala Ala Ala Arg Ser Gly
1               5

<210> SEQ ID NO 65
<211> LENGTH: 8
<212> TYPE: PRT
<213> ORGANISM: Artificial Sequence
<220> FEATURE:
<223> OTHER INFORMATION: Synthesized Peptide

<400> SEQUENCE: 65
```

```
Gly Ala Ala Ala Ala Arg Ser Gly
1               5

<210> SEQ ID NO 66
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 66

Gly Ala Ala Arg
1

<210> SEQ ID NO 67
<211> LENGTH: 16
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is an amino acid residue whose side chain
      is positively charged under physiological conditions, preferably
      O (ornithine) and wherein the N-Termiuns is preferably guanidated
<220> FEATURE:
<221> NAME/KEY: misc_feature
<222> LOCATION: (2)..(2)
<223> OTHER INFORMATION: Xaa is an amino acid residue having an amino
      group in the side chain
<220> FEATURE:
<221> NAME/KEY: misc_feature
<222> LOCATION: (4)..(4)
<223> OTHER INFORMATION: Xaa is an amino acid residue whose side chain
      is positively charged under physiological conditions, preferably
      R (arginine)
<220> FEATURE:
<221> NAME/KEY: misc_feature
<222> LOCATION: (10)..(10)
<223> OTHER INFORMATION: Xaa is an amino acid residue whose side chain
      is positively charged under physiological conditions, preferably
      R (arginine)
<220> FEATURE:
<221> NAME/KEY: misc_feature
<222> LOCATION: (11)..(11)
<223> OTHER INFORMATION: Xaa is proline or a proline derivative
<220> FEATURE:
<221> NAME/KEY: misc_feature
<222> LOCATION: (16)..(16)
<223> OTHER INFORMATION: Pro is a proline with a C-Terminus or a proline
      bound to a peptide having from 1 to 4 amino acids residues,
      preferably a dipeptide havung the sequnece RL (Arg-Leu)

<400> SEQUENCE: 67

Xaa Xaa Asn Xaa Pro Val Tyr Ile Pro Xaa Xaa Arg Pro Pro His Pro
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is an amino acid residue whose side chain
      is positively charged under physiological conditions, preferably
      O (ornithine) and wherein the N-Termiuns is preferably guanidated
<220> FEATURE:
<221> NAME/KEY: misc_feature
<222> LOCATION: (3)..(3)
```

```
<223> OTHER INFORMATION: Xaa is an amino acid residue having an amino
      group in the side chain
<220> FEATURE:
<221> NAME/KEY: misc_feature
<222> LOCATION: (4)..(4)
<223> OTHER INFORMATION: Xaa is an amino acid residue whose side chain
      is positively charged under physiological conditions, preferably
      R (arginine)
<220> FEATURE:
<221> NAME/KEY: misc_feature
<222> LOCATION: (10)..(10)
<223> OTHER INFORMATION: Xaa is an amino acid residue whose side chain
      is positively charged under physiological conditions, preferably
      R (arginine)
<220> FEATURE:
<221> NAME/KEY: misc_feature
<222> LOCATION: (11)..(11)
<223> OTHER INFORMATION: Xaa is proline or a proline derivative
<220> FEATURE:
<221> NAME/KEY: misc_feature
<222> LOCATION: (16)..(16)
<223> OTHER INFORMATION: Pro is a proline with a C-Terminus or a
      proline bound to a peptide having from 1 to 4 amino acids
      residues, preferably a dipeptide havung the sequnece RL (Arg-Leu)

<400> SEQUENCE: 68

Xaa Asn Xaa Xaa Pro Val Tyr Ile Pro Xaa Xaa Arg Pro Pro His Pro
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is an amino acid residue having an amino
      group in the side chain and wherein the N-Termiuns is preferably
      guanidated
<220> FEATURE:
<221> NAME/KEY: misc_feature
<222> LOCATION: (4)..(4)
<223> OTHER INFORMATION: Xaa is an amino acid residue whose side chain
      is positively charged under physiological conditions, preferably
      R (arginine)
<220> FEATURE:
<221> NAME/KEY: misc_feature
<222> LOCATION: (10)..(10)
<223> OTHER INFORMATION: Xaa is an amino acid residue whose side chain
      is positively charged under physiological conditions, preferably
      R (arginine)
<220> FEATURE:
<221> NAME/KEY: misc_feature
<222> LOCATION: (11)..(11)
<223> OTHER INFORMATION: Xaa is proline or a proline derivative
<220> FEATURE:
<221> NAME/KEY: misc_feature
<222> LOCATION: (16)..(16)
<223> OTHER INFORMATION: Pro is a proline with a C-Terminus or a proline
      bound to a peptide having from 1 to 4 amino acids residues,
      preferably a dipeptide havung the sequnece RL (Arg-Leu)

<400> SEQUENCE: 69

Xaa Asn Asn Xaa Pro Val Tyr Ile Pro Xaa Xaa Arg Pro Pro His Pro
1               5                   10                  15

<210> SEQ ID NO 70
<211> LENGTH: 5
<212> TYPE: PRT
<213> ORGANISM: Artificial Sequence
<220> FEATURE:
<223> OTHER INFORMATION: Synthesized Peptide
<220> FEATURE:
```

```
<221> NAME/KEY: misc_feature
<222> LOCATION: (2)..(2)
<223> OTHER INFORMATION: Xaa are 1 to 6, preferably 1, 2, 3 or 4 amino
      acid residues selecetd from Ala, Gly or Ser

<400> SEQUENCE: 70

Gly Xaa Arg Ser Gly
1               5

<210> SEQ ID NO 71
<211> LENGTH: 19
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is an amino acid residue having a
      non-polar, hydrophobic side chain or an amino acid residue whose
      side chain is positively charged under physiological conditions,
      having a positive net charge or a side chain tht is positively
      charged under
<220> FEATURE:
<221> NAME/KEY: misc_feature
<222> LOCATION: (2)..(2)
<223> OTHER INFORMATION: Asp is aspartic acid or glutamic acid residue
      or any desired residue
<220> FEATURE:
<221> NAME/KEY: misc_feature
<222> LOCATION: (3)..(3)
<223> OTHER INFORMATION: Lys is a residue having apositive net charge
      or a side chain that is positively charged under physiological
      conditions, preferably Lys or Arg
<220> FEATURE:
<221> NAME/KEY: misc_feature
<222> LOCATION: (4)..(4)
<223> OTHER INFORMATION: Pro is selceted independetly from proline or
      proline derivative or hydroxyproline and hydroxyproline drivatives
      or replaced by any desired residue
<220> FEATURE:
<221> NAME/KEY: misc_feature
<222> LOCATION: (5)..(5)
<223> OTHER INFORMATION: Pro is selceted independetly from proline or
      proline derivative or hydroxyproline and hydroxyproline drivatives
      or replaced by any desired residue
<220> FEATURE:
<221> NAME/KEY: misc_feature
<222> LOCATION: (7)..(7)
<223> OTHER INFORMATION: Leu is selceted independetly from residues
      having a non-polar, hydrophobic side chain, preferably Leu, Ile,
      Val and tert-Leu
<220> FEATURE:
<221> NAME/KEY: misc_feature
<222> LOCATION: (8)..(8)
<223> OTHER INFORMATION: Pro is selceted independetly from proline or
      proline derivative or hydroxyproline and hydroxyproline drivatives
      or replaced by any desired residue
<220> FEATURE:
<221> NAME/KEY: misc_feature
<222> LOCATION: (10)..(10)
<223> OTHER INFORMATION: Pro is selceted independetly from proline or
      proline derivative or hydroxyproline and hydroxyproline drivatives
      or or replaced by any desired residue
<220> FEATURE:
<221> NAME/KEY: misc_feature
<222> LOCATION: (11)..(11)
<223> OTHER INFORMATION: Xaa is selceted independetly from residues
      having a positive net charge or a side chain that is positively
      charged under physiological conditions
<220> FEATURE:
<221> NAME/KEY: misc_feature
<222> LOCATION: (12)..(12)
<223> OTHER INFORMATION: Pro is selceted independetly from proline or
      proline derivative or hydroxyproline and hydroxyproline drivatives
      or replaced by any desired residue
<220> FEATURE:
```

```
<221> NAME/KEY: misc_feature
<222> LOCATION: (13)..(13)
<223> OTHER INFORMATION: Pro is selceted independetly from proline or
      proline derivative or hydroxyproline and hydroxyproline drivatives
      or Arg or replaced by any desired residue
<220> FEATURE:
<221> NAME/KEY: misc_feature
<222> LOCATION: (14)..(14)
<223> OTHER INFORMATION: Arg is Arg or Pro
<220> FEATURE:
<221> NAME/KEY: misc_feature
<222> LOCATION: (15)..(15)
<223> OTHER INFORMATION: Xaa is a radical having a positive net charge
      or a side chain that is positively charged under physiological
      conditions or proline or a proline derivative
<220> FEATURE:
<221> NAME/KEY: misc_feature
<222> LOCATION: (16)..(16)
<223> OTHER INFORMATION: Ile is selceted independetly from residues
      having a non-polar, hydrophobic side chain, preferably Leu, Ile,
      Val and tert-Leu
<220> FEATURE:
<221> NAME/KEY: misc_feature
<222> LOCATION: (17)..(17)
<223> OTHER INFORMATION: Tyr is Tyr or replaced by any desired residue
<220> FEATURE:
<221> NAME/KEY: misc_feature
<222> LOCATION: (19)..(19)
<223> OTHER INFORMATION: Xaa is selceted independetly from residues
      having a positive net charge or a side chain that is positively
      charged under physiological conditions, wherein the amino acid
      have a free C-Terminal carboxyl group or a modified C-terminal
      carboxyl group

<400> SEQUENCE: 71

Xaa Asp Lys Pro Pro Tyr Leu Pro Arg Pro Xaa Pro Pro Arg Xaa Ile
1               5                   10                  15

Tyr Asn Xaa

<210> SEQ ID NO 72
<211> LENGTH: 20
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is an amino acid residue having a
      non-polar, hydrophobic side chain or an amino acid residue whose
      side chain is positively charged under physiological conditions,
      having a positive net charge or a side chain tht is positively
      charged under
<220> FEATURE:
<221> NAME/KEY: misc_feature
<222> LOCATION: (2)..(2)
<223> OTHER INFORMATION: Asp is aspartic acid or glutamic acid residue
      or any desired residue
<220> FEATURE:
<221> NAME/KEY: misc_feature
<222> LOCATION: (3)..(3)
<223> OTHER INFORMATION: Lys is a residue having apositive net charge
      or a side chain that is positively charged under physiological
      conditions, preferably Lys or Arg
<220> FEATURE:
<221> NAME/KEY: misc_feature
<222> LOCATION: (4)..(4)
<223> OTHER INFORMATION: Pro is selceted independetly from proline or
      proline derivative or hydroxyproline and hydroxyproline drivatives
      or replaced by any desired residue
<220> FEATURE:
<221> NAME/KEY: misc_feature
<222> LOCATION: (5)..(5)
<223> OTHER INFORMATION: Pro is selceted independetly from proline or
      proline derivative or hydroxyproline and hydroxyproline drivatives
      or replaced by any desired residue
```

```
<220> FEATURE:
<221> NAME/KEY: misc_feature
<222> LOCATION: (7)..(7)
<223> OTHER INFORMATION: Leu is selceted indepndetly from residues
      having a non-polar, hydrophobic side chain, preferably Leu, Ile,
      Val and tert-Leu
<220> FEATURE:
<221> NAME/KEY: misc_feature
<222> LOCATION: (8)..(8)
<223> OTHER INFORMATION: Pro is selceted indepndetly from proline or
      proline derivative or hydroxyproline and hydroxyproline drivatives
      or replaced by any desired residue
<220> FEATURE:
<221> NAME/KEY: misc_feature
<222> LOCATION: (10)..(10)
<223> OTHER INFORMATION: Pro is selceted indepndetly from proline or
      proline derivative or hydroxyproline and hydroxyproline drivatives
      or or replaced by any desired residue
<220> FEATURE:
<221> NAME/KEY: misc_feature
<222> LOCATION: (11)..(11)
<223> OTHER INFORMATION: Xaa is selceted indepndetly from residues
      having a positive net charge or a side chain that is positively
      charged under physiological conditions
<220> FEATURE:
<221> NAME/KEY: misc_feature
<222> LOCATION: (12)..(12)
<223> OTHER INFORMATION: Pro is selceted indepndetly from proline or
      proline derivative or hydroxyproline and hydroxyproline drivatives
      or replaced by any desired residue
<220> FEATURE:
<221> NAME/KEY: misc_feature
<222> LOCATION: (13)..(13)
<223> OTHER INFORMATION: Pro is selceted indepndetly from proline or
      proline derivative or hydroxyproline and hydroxyproline drivatives
      or Arg or replaced by any desired residue
<220> FEATURE:
<221> NAME/KEY: misc_feature
<222> LOCATION: (14)..(14)
<223> OTHER INFORMATION: Arg is Arg or Pro
<220> FEATURE:
<221> NAME/KEY: misc_feature
<222> LOCATION: (15)..(15)
<223> OTHER INFORMATION: Xaa is a radical having a positive net charge
      or a side chain that is positively charged under physiological
      conditions or proline or a proline derivative
<220> FEATURE:
<221> NAME/KEY: misc_feature
<222> LOCATION: (16)..(16)
<223> OTHER INFORMATION: Ile is selceted indepndetly from residues
      having a non-polar, hydrophobic side chain, preferably Leu, Ile,
      Val and tert-Leu
<220> FEATURE:
<221> NAME/KEY: misc_feature
<222> LOCATION: (17)..(17)
<223> OTHER INFORMATION: Pro is selceted indepndetly from proline or
      proline derivative or hydroxyproline and hydroxyproline drivatives
      or replaced by any desired residue
<220> FEATURE:
<221> NAME/KEY: misc_feature
<222> LOCATION: (20)..(20)
<223> OTHER INFORMATION: Xaa is selceted indepndetly from residues
      having a positive net charge or a side chain that is positively
      charged under physiological conditions, wherein the amino acid
      have a free C-Terminal carboxyl group or a modified C-terminal
      carboxyl group

<400> SEQUENCE: 72

Xaa Asp Lys Pro Pro Tyr Leu Pro Arg Pro Xaa Pro Pro Arg Xaa Ile
1               5                   10                  15

Tyr Asn Asn Xaa
            20

<210> SEQ ID NO 73
<211> LENGTH: 19
<212> TYPE: PRT
```

-continued

```
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is an amino acid residue having a
      non-polar, hydrophobic side chain or an amino acid residue whose
      side chain is positively charged under physiological conditions,
      having a positive net charge or a side chain tht is positively
      charged under
<220> FEATURE:
<221> NAME/KEY: misc_feature
<222> LOCATION: (2)..(2)
<223> OTHER INFORMATION: Asp is aspartic acid or glutamic acid residue
      or any desired residue
<220> FEATURE:
<221> NAME/KEY: misc_feature
<222> LOCATION: (3)..(3)
<223> OTHER INFORMATION: Lys is a residue having apositive net charge
      or a side chain that is positively charged under physiological
      conditions, preferably Lys or Arg
<220> FEATURE:
<221> NAME/KEY: misc_feature
<222> LOCATION: (4)..(4)
<223> OTHER INFORMATION: Pro is selceted indepndetly from proline or
      proline derivative or hydroxyproline and hydroxyproline drivatives
      or replaced by any desired residue
<220> FEATURE:
<221> NAME/KEY: misc_feature
<222> LOCATION: (5)..(5)
<223> OTHER INFORMATION: Pro is selceted indepndetly from proline or
      proline derivative or hydroxyproline and hydroxyproline drivatives
      or replaced by any desired residue
<220> FEATURE:
<221> NAME/KEY: misc_feature
<222> LOCATION: (7)..(7)
<223> OTHER INFORMATION: Leu is selceted indepndetly from residues
      having a non-polar, hydrophobic side chain, preferably Leu, Ile,
      Val and tert-Leu
<220> FEATURE:
<221> NAME/KEY: misc_feature
<222> LOCATION: (8)..(8)
<223> OTHER INFORMATION: Pro is selceted indepndetly from proline or
      proline derivative or hydroxyproline and hydroxyproline drivatives
      or replaced by any desired residue
<220> FEATURE:
<221> NAME/KEY: misc_feature
<222> LOCATION: (10)..(10)
<223> OTHER INFORMATION: Pro is selceted indepndetly from proline or
      proline derivative or hydroxyproline and hydroxyproline drivatives
      or or replaced by any desired residue
<220> FEATURE:
<221> NAME/KEY: misc_feature
<222> LOCATION: (11)..(11)
<223> OTHER INFORMATION: Xaa is selceted indepndetly from residues
      having a positive net charge or a side chain that is positively
      charged under physiological conditions
<220> FEATURE:
<221> NAME/KEY: misc_feature
<222> LOCATION: (12)..(12)
<223> OTHER INFORMATION: Pro is selceted indepndetly from proline or
      proline derivative or hydroxyproline and hydroxyproline drivatives
      or replaced by any desired residue
<220> FEATURE:
<221> NAME/KEY: misc_feature
<222> LOCATION: (13)..(13)
<223> OTHER INFORMATION: Pro is selceted indepndetly from proline or
      proline derivative or hydroxyproline and hydroxyproline drivatives
      or Arg or replaced by any desired residue
<220> FEATURE:
<221> NAME/KEY: misc_feature
<222> LOCATION: (14)..(14)
<223> OTHER INFORMATION: Arg is Arg or Pro
<220> FEATURE:
<221> NAME/KEY: misc_feature
<222> LOCATION: (15)..(15)
<223> OTHER INFORMATION: Xaa is a radical having a positive net charge
      or a side chain that is positively charged under physiological
```

```
    conditions or proline or a proline derivative
<220> FEATURE:
<221> NAME/KEY: misc_feature
<222> LOCATION: (16)..(16)
<223> OTHER INFORMATION: Ile is selceted independetly from residues
      having a non-polar, hydrophobic side chain, preferably Leu, Ile,
      Val and tert-Leu
<220> FEATURE:
<221> NAME/KEY: misc_feature
<222> LOCATION: (17)..(17)
<223> OTHER INFORMATION: Pro is selceted independetly from proline or
      proline derivative or hydroxyproline and hydroxyproline drivatives
      or replaced by any desired residue
<220> FEATURE:
<221> NAME/KEY: misc_feature
<222> LOCATION: (19)..(19)
<223> OTHER INFORMATION: Xaa is selceted independetly from residues
      having a positive net charge or a side chain that is positively
      charged under physiological conditions, wherein the amino acid
      have a free C-Terminal carboxyl group or a modified C-terminal
      carboxyl group

<400> SEQUENCE: 73

Xaa Asp Lys Pro Pro Tyr Leu Pro Arg Pro Xaa Pro Pro Arg Xaa Ile
1               5                   10                  15

Pro Asn Xaa

<210> SEQ ID NO 74
<211> LENGTH: 3
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (2)..(2)
<223> OTHER INFORMATION: Xaa are  1, 2 or 3 or 4 amino acid residues
      selecetd from Ala, Gly or Ser

<400> SEQUENCE: 74

Gly Xaa Arg
1

<210> SEQ ID NO 75
<211> LENGTH: 21
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is an amino acid residue having a
      non-polar, hydrophobic side chain or an amino acid residue whose
      side chain is positively charged under physiological conditions,
      having a positive net charge or a side chain tht is positively
      charged under
<220> FEATURE:
<221> NAME/KEY: misc_feature
<222> LOCATION: (11)..(11)
<223> OTHER INFORMATION: Xaa is selceted independetly from residues
      having a positive net charge or a side chain that is positively
      charged under physiological conditions
<220> FEATURE:
<221> NAME/KEY: misc_feature
<222> LOCATION: (15)..(15)
<223> OTHER INFORMATION: Xaa is a radical having a positive net charge
      or a side chain that is positively charged under physiological
      conditions or proline or a proline derivative
<220> FEATURE:
<221> NAME/KEY: misc_feature
<222> LOCATION: (19)..(19)
<223> OTHER INFORMATION: Xaa is selceted independetly from residues
      having a positive net charge or a side chain that is positively
```

```
       charged under physiological conditions
<220> FEATURE:
<221> NAME/KEY: misc_feature
<222> LOCATION: (20)..(20)
<223> OTHER INFORMATION: Xaa is selected from  proline or a proline
      derivative or a neutral residue having a polar side chain
<220> FEATURE:
<221> NAME/KEY: misc_feature
<222> LOCATION: (21)..(21)
<223> OTHER INFORMATION: Xaa is selected from  proline or a proline
      derivative or a neutral residue having a polar side chain or a
      hydrophobic residue or a branched linker, which contains a
      plurality of peptide units

<400> SEQUENCE: 75

Xaa Asp Lys Pro Pro Tyr Leu Pro Arg Pro Xaa Pro Pro Arg Xaa Ile
1               5                   10                  15

Tyr Asn Xaa Xaa Xaa
            20

<210> SEQ ID NO 76
<211> LENGTH: 20
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa is an amino acid residue having a
      non-polar, hydrophobic side chain or an amino acid residue whose
      side chain is positively charged under physiological conditions,
      having a positive net charge or a side chain tht is positively
      charged under
<220> FEATURE:
<221> NAME/KEY: misc_feature
<222> LOCATION: (11)..(11)
<223> OTHER INFORMATION: Xaa is selceted independetly from residues
      having a positive net charge or a side chain that is positively
      charged under physiological conditions
<220> FEATURE:
<221> NAME/KEY: misc_feature
<222> LOCATION: (15)..(15)
<223> OTHER INFORMATION: Xaa is a radical having a positive net charge
      or a side chain that is positively charged under physiological
      conditions or proline or a proline derivative
<220> FEATURE:
<221> NAME/KEY: misc_feature
<222> LOCATION: (19)..(19)
<223> OTHER INFORMATION: Xaa is selceted independetly from residues
      having a positive net charge or a side chain that is positively
      charged under physiological conditions
<220> FEATURE:
<221> NAME/KEY: misc_feature
<222> LOCATION: (20)..(20)
<223> OTHER INFORMATION: Xaa is selected from  proline or a proline
      derivative or a neutral residue having a polar side chain

<400> SEQUENCE: 76

Xaa Asp Lys Pro Pro Tyr Leu Pro Arg Pro Xaa Pro Pro Arg Xaa Ile
1               5                   10                  15

Tyr Asn Xaa Xaa
            20

<210> SEQ ID NO 77
<211> LENGTH: 20
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
```

```
<223> OTHER INFORMATION: Xaa is an amino acid residue having a
      non-polar, hydrophobic side chain or an amino acid residue whose
      side chain is positively charged under physiological conditions,
      having a positive net charge or a side chain tht is positively
      charged under
<220> FEATURE:
<221> NAME/KEY: misc_feature
<222> LOCATION: (11)..(11)
<223> OTHER INFORMATION: Xaa is selceted independetly from residues
      having a positive net charge or a side chain that is positively
      charged under physiological conditions
<220> FEATURE:
<221> NAME/KEY: misc_feature
<222> LOCATION: (15)..(15)
<223> OTHER INFORMATION: Xaa is a radical having a positive net charge
      or a side chain that is positively charged under physiological
      conditions or proline or a proline derivative
<220> FEATURE:
<221> NAME/KEY: misc_feature
<222> LOCATION: (19)..(19)
<223> OTHER INFORMATION: Xaa is selceted independetly from residues
      having a positive net charge or a side chain that is positively
      charged under physiological conditions
<220> FEATURE:
<221> NAME/KEY: misc_feature
<222> LOCATION: (20)..(20)
<223> OTHER INFORMATION: Xaa is selected from  proline or a proline
      derivative or a neutral residue having a polar side chain or a
      hydrophobic residue or a branched linker, which contains a
      plurality of peptide units

<400> SEQUENCE: 77

Xaa Asp Lys Pro Pro Tyr Leu Pro Arg Pro Xaa Pro Pro Arg Xaa Ile
1               5                   10                  15

Tyr Asn Xaa Xaa
            20

<210> SEQ ID NO 78
<211> LENGTH: 18
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (1)..(1)
<220> FEATURE:
<221> NAME/KEY: MISC_FEATURE
<222> LOCATION: (1)..(1)
<223> OTHER INFORMATION: Xaa is N-guanido-ornithine with N-PEG750
      bound to Orn delta-NH2 via linker

<400> SEQUENCE: 78

Xaa Asn Asn Arg Pro Val Tyr Ile Pro Arg Pro Arg Pro Pro His Pro
1               5                   10                  15

Arg Leu

<210> SEQ ID NO 79
<211> LENGTH: 18
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (1)..(1)
<223> OTHER INFORMATION: Xaa is N-guanido-ornithine with N-PEG5000
      bound to Orn delta-NH2 via linker

<400> SEQUENCE: 79

Xaa Asn Asn Arg Pro Val Tyr Ile Pro Arg Pro Arg Pro Pro His Pro
1               5                   10                  15
```

Arg Leu

<210> SEQ ID NO 80
<211> LENGTH: 18
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (1)..(1)
<223> OTHER INFORMATION: Xaa is N-guanido-ornithine
<220> FEATURE:
<221> NAME/KEY: MISC_FEATURE
<222> LOCATION: (2)..(2)
<223> OTHER INFORMATION: Xaa is Orn with N-PEG750 bound to Orn
      delta-NH2 via linker

<400> SEQUENCE: 80

Xaa Xaa Asn Arg Pro Val Tyr Ile Pro Arg Pro Arg Pro Pro His Pro
1               5                   10                  15

Arg Leu

<210> SEQ ID NO 81
<211> LENGTH: 18
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (1)..(1)
<223> OTHER INFORMATION: Xaa is N-guanido-ornithine
<220> FEATURE:
<221> NAME/KEY: MISC_FEATURE
<222> LOCATION: (2)..(2)
<223> OTHER INFORMATION: Xaa is Orn with N-PEG5000 bound to Orn
      delta-NH2 via linker

<400> SEQUENCE: 81

Xaa Xaa Asn Arg Pro Val Tyr Ile Pro Arg Pro Arg Pro Pro His Pro
1               5                   10                  15

Arg Leu

<210> SEQ ID NO 82
<211> LENGTH: 18
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (1)..(1)
<223> OTHER INFORMATION: Xaa is N-guanido-ornithine
<220> FEATURE:
<221> NAME/KEY: MISC_FEATURE
<222> LOCATION: (3)..(3)
<223> OTHER INFORMATION: Xaa is Orn with N-PEG750 bound to Orn
      delta-NH2 via linker

<400> SEQUENCE: 82

Xaa Asn Xaa Arg Pro Val Tyr Ile Pro Arg Pro Arg Pro Pro His Pro
1               5                   10                  15

Arg Leu

<210> SEQ ID NO 83
<211> LENGTH: 18
<212> TYPE: PRT

```
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (1)..(1)
<223> OTHER INFORMATION: Xaa is N-guanido-ornithine
<220> FEATURE:
<221> NAME/KEY: MISC_FEATURE
<222> LOCATION: (3)..(3)
<223> OTHER INFORMATION: Xaa is Orn with N-PEG750 bound to Orn
      delta-NH2 via linker

<400> SEQUENCE: 83

Xaa Asn Xaa Arg Pro Val Tyr Ile Pro Arg Pro Arg Pro Pro His Pro
1               5                   10                  15

Arg Leu
```

What is claimed is:

1. A modified peptide containing one of the following sequences:

NT-$X_1$-$D_2$-$K_3$-$P_4$-$P_5$-$Y_6$-$L_7$-$P_8$-$R_9$-$P_{10}$-$X_2$-$P_{12}$-$P_{13}$-$R_{14}$-$X_3$-$I_{16}$-$Y_{17}$-$N_{18}$-$X_4$-CT

NT-$X_1$-$D_2$-$K_3$-$P_4$-$P_5$-$Y_6$-$L_7$-$P_8$-$R_9$-$P_{10}$-$X_2$-$P_{12}$-$P_{13}$-$R_{14}$-$X_3$-$I_{16}$-$Y_{17}$-$N_{18}$-$N_{19}$-$X_4$-CT

NT-$X_1$-$D_2$-$K_3$-$P_4$-$P_5$-$Y_6$-$L_7$-$P_8$-$R_9$-$P_{10}$-$X_2$-$P_{12}$-$P_{13}$-$R_{14}$-$X_3$-$I_{16}$-$P_{17}$-$N_{18}$-$X_4$-CT $X_1$ is a residue having a non-polar, hydrophobic side chain or an amino acid residue whose side chain is positively charged under physiological conditions, having a positive net charge or a side chain that is positively charged under physiological conditions;

$D_2$ is an aspartic acid or glutamic acid residue, $K_3$ is a residue having a positive net charge or a side chain that is positively charged under physiological conditions, $X_2$ and $X_4$ are selected independently of one another from residues having a positive net charge or a side chain that is positively charged under physiological conditions;

$X_3$ is a residue having a positive net charge or a side chain that is positively charged under physiological conditions or proline or a proline derivative;

$L_7$ and $I_{16}$ are selected independently of one another from residues having a non-polar, hydrophobic side chain, $Y_6$ and $Y_{17}$ are each tyrosine, $R_9$ and $R_{14}$ are each arginine, $N_{18}$ and $N_{19}$ are each asparagine or glutamine, $P_4$, $P_5$, $P_8$, $P_{10}$, $P_{12}$, $P_{13}$ and $P_{17}$ are selected independently of one another from proline and proline derivatives or hydroxyproline and hydroxyproline derivatives, wherein $P_{13}$ and $R_{14}$ are optionally interchanged, and/or optionally one or two of the residues selected from $D_2$, $P_4$, $P_5$, $P_8$, $P_{10}$, $P_{12}$, $P_{13}$, $P_{17}$ and $Y_{17}$ are replaced by any desired residue, NT is the N-terminus of the amino acid $X_1$, CT is the free or modified C-terminus of the amino acid $X_4$, wherein a linear or branched polyethylene glycol polymer chain is bonded to NT via a peptide linker, and wherein the peptide linker is GAAR (SEQ ID No. 66).

2. The modified peptide according to claim 1 containing one of the following sequences:

```
                                               (SEQ ID No. 12)
VDKPPYLPRPRPPROIYNO-NH2
or
                                               (SEQ ID No. 13)
VDKPPYLPRPRPHypRHypTleYNO-NH2
where O = L-ornithine, Hyp = L-4-hydroxyproline,
TLe = L-t-leucine (L-t-butyliglycine),
``` wherein the linear or branched polyethylene glycol polymer chain is bonded via the peptide linker to the N-terminal amino acid residue V.

3. The modified peptide according to claim 1, wherein the polyethylene glycol polymer chain has a molecular weight of from 500 to 40,000 Da.

4. The modified peptide according to claim 1 in the form of an antibiotic, a disinfectant or cleaning agent, a preservative or an additive in a packaging material.

5. The modified peptide according to claim 4 in the form of an agent for the treatment of microbial, bacterial or fungal infections or contamination with microbes, bacteria or fungi.

6. The modified peptide according to claim 1, wherein $K_3$ is lysine or arginine.

7. The modified peptide according to claim 1, wherein $L_7$ and $I_{16}$ are selected independently of one another from leucine, isoleucine, and valine.

8. The modified peptide according to claim 1, wherein the N-terminus of the amino acid $X_1$ is modified by being acetylated, formylated or guanidated.

* * * * *